(12) United States Patent
Lau et al.

(10) Patent No.: US 9,930,842 B2
(45) Date of Patent: Apr. 3, 2018

(54) BIOREACTOR

(71) Applicant: Nanyang Technological University, Singapore (SG)

(72) Inventors: Wai Man Lau, Singapore (SG); Seri Lee, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 397 days.

(21) Appl. No.: 14/366,252

(22) PCT Filed: Dec. 12, 2012

(86) PCT No.: PCT/SG2012/000469
§ 371 (c)(1),
(2) Date: Jun. 17, 2014

(87) PCT Pub. No.: WO2013/095300
PCT Pub. Date: Jun. 27, 2013

(65) Prior Publication Data
US 2014/0331552 A1    Nov. 13, 2014

Related U.S. Application Data

(60) Provisional application No. 61/577,547, filed on Dec. 19, 2011.

(51) Int. Cl.
*A01G 33/00* (2006.01)
*C12M 1/00* (2006.01)
(Continued)

(52) U.S. Cl.
CPC .............. *A01G 33/00* (2013.01); *C12M 21/02* (2013.01); *C12M 23/06* (2013.01); *C12M 23/34* (2013.01);
(Continued)

(58) Field of Classification Search
CPC ...... C12M 21/02; C12M 23/06; C12M 23/22; C12M 23/24; C12M 31/00; C12M 31/02;
(Continued)

(56) References Cited

U.S. PATENT DOCUMENTS 5,320,963 A    6/1994 Knaack et al.
5,958,761 A    9/1999 Yogev et al.
(Continued)

FOREIGN PATENT DOCUMENTS

CN    100374539 C    3/2008
DE    2037903 A1 *    2/1971    ............ C12M 23/34
(Continued)

OTHER PUBLICATIONS

Singh et al. Jan. 10, 2007, Wiley InterScience, Flow modeling in a novel non-perfusion conical bioreactor, 1291-1299.*
(Continued)

*Primary Examiner* — Kristen C Hayes
*Assistant Examiner* — Christopher D Hutchens
(74) *Attorney, Agent, or Firm* — Seed IP Law Group LLP

(57) ABSTRACT

According to embodiments of the present invention, a bioreactor for growing photoautotrophic organisms is provided. The bioreactor includes a vessel configured to receive the photoautotrophic organisms, the vessel having a longitudinal axis, which a circumferential wall extends around said axis, wherein said circumferential wall is translucent so as to enable light to enter the vessel from the outside for acting on the photoautotrophic organisms, wherein a device for providing an uneven distribution of the light intensity within said vessel along said axis is provided.

18 Claims, 12 Drawing Sheets

(51) Int. Cl.
*C12M 1/12* (2006.01)
*C12M 1/08* (2006.01)

(52) U.S. Cl.
CPC ............ *C12M 23/58* (2013.01); *C12M 27/24* (2013.01); *C12M 31/04* (2013.01); *C12M 31/08* (2013.01); *C12M 41/06* (2013.01); *C12M 41/10* (2013.01); *C12M 47/02* (2013.01)

(58) Field of Classification Search
CPC ...... C12M 31/04; C12M 31/06; C12M 31/08; A01G 33/00; C12N 1/12; A01H 4/001
See application file for complete search history.

(56) References Cited

U.S. PATENT DOCUMENTS

| | | | |
|---|---|---|---|
| 6,509,188 | B1 | 1/2003 | Trösch et al. |
| D523,693 | S * | 6/2006 | Bodum ............................ D7/509 |
| D655,982 | S * | 3/2012 | Liu ................................. D7/509 |
| 2009/0155864 | A1 * | 6/2009 | Bauer .................... C12M 21/02 435/134 |
| 2009/0205638 | A1 | 8/2009 | Corcoran |
| 2012/0295248 | A1 * | 11/2012 | Cheng ................. B01F 3/04609 435/3 |
| 2014/0030762 | A1 * | 1/2014 | Deplano ................ C12M 21/08 435/70.3 |

FOREIGN PATENT DOCUMENTS

| | | | | |
|---|---|---|---|---|
| DE | 102007050484 | A1 * | 11/2008 | ............. C12M 21/02 |
| RU | 2203863 | C2 * | 5/2003 | |
| WO | 98/11199 | A1 | 3/1998 | |
| WO | 02/086053 | A1 | 10/2002 | |
| WO | 2007/070452 | A1 | 6/2007 | |
| WO | 2009/147222 | A1 | 12/2009 | |
| WO | 2010/138657 | A1 | 12/2010 | |
| WO | WO 2012019206 | A1 * | 2/2012 | ............. A01G 33/00 |

OTHER PUBLICATIONS

Chen et al., "Lumostatic strategy for microalgae cultivation utilizing image analysis and chlorophyll α content as design parameters," *Bioresource Technology* 102:6005-6012, 2011.

Hossain et al., "Determination of Actual Object Size Distribution from Direct Imaging," *Ind. Eng. Chem. Res.* 48:10136-10146, 2009.

Choi, Su-Lim et al., "Lumostatic operation of bubble column photobioreactors for *Haematococcus pluvialis* cultures using a specific light uptake rate as a control parameter," Enzyme and Microbial Technology, vol. 33, pp. 403-409, 2003.

Office Action in Chinese Application No. 201280067638.6, dated Mar. 24, 2015, w/ English Translation, 21 pages.

* cited by examiner

—●— Chl a (mg/mg)   —□— Q (μmol/cell·s)

—●— Chl a (mg/mg)   —□— Q (μmol/cell·s)

BIOREACTOR

CROSS-REFERENCE TO RELATED APPLICATION

This application claims the benefit of priority of U.S. provisional application No. 61/577,547, filed 19 Dec. 2011, the content of it being hereby incorporated by reference in its entirety for all purposes.

TECHNICAL FIELD

Various embodiments relate to a bioreactor.

BACKGROUND

Crude oil reserve is rapidly depleting. At present, cultivation of photoautotrophic organisms such as microalgae has been identified as a potential strategy to address the aforementioned major concerns. Microalgae may be used as an alternative feedstock for biofuel production. Unlike the rapidly depleting cruel oil reserve, it is renewable and provides rapid growth. With high lipid triglyceride content up to 80% of the dry weight and rapid exponential growth rates, microalgae potentially offer high oil productivities at low raw material costs, in contrast to high vegetable oil costs commonly observed in biodiesel production. In addition to biodiesel production, microalgae are presently cultured to produce materials for health supplements, aquaculture feed, pigment components, polyunsaturated fatty acids and other fine chemicals, while the waste cellular debris, collected after harvesting of valuable lipids and materials, can be converted into alternative biofuel forms including biomethane, bioethanol and biohydrogen.

Cultivation of microalgae can be classified under two major systems: open system (e.g. raceway ponds) or closed systems (e.g. photobioreactors). Presently, open systems remain the more popular cultivation system industrially due to the low cost associated with building and operation of the open systems. However, the key disadvantage of open raceway ponds is that biomass areal and volumetric productivity is low. In addition, raceway ponds are susceptible to contamination and are poorly mixed. Therefore, they are unable to utilize light efficiently and use carbon less effectively than closed systems.

In contrast, photobioreactors enable single-species culture to be produced with a higher volumetric productivity, and photobioreactors have been used for industrial production of large quantities of microalgal biomass. Furthermore, in order for high-value compounds to be produced, it mandates the use of monocultures in controlled cultivation systems. A conventional photobioreactor is capable of sustaining higher biomass concentration than that obtained in open raceway ponds. This hence minimizes the size requirement of the reactor, and simultaneously lowers the downstream processing costs.

Tubular photobioreactors with small diameters are currently employed in large-scale production of microalgae. While small diameter tubes are found to maximize the utilization of solar light capture, strong turbulent streaming is required, and additionally, the high pumping pressure required for maintaining the necessary flow rate through the length of the tube render the system more expensive and less practicable for large scale operations. Furthermore, small tube diameters have also been found to increase bio-fouling, reduce control over salt precipitation, and possess strong oxygen tension that is disadvantageous in general for actively photosynthesizing systems.

SUMMARY

According to an aspect of the invention, a bioreactor for growing photoautotrophic organisms is provided. The bioreactor may include a vessel configured to receive the photoautotrophic organisms, the vessel having a longitudinal axis, which a circumferential wall extends around said axis, wherein said circumferential wall is translucent so as to enable light to enter the vessel from the outside for acting on the photoautotrophic organisms, wherein a device for providing an uneven distribution of the light intensity within said vessel along said axis is provided.

Said device for providing an uneven distribution of the light intensity may include said circumferential wall such that the translucent surface varies along said axis. The circumference of said circumferential wall may vary along said axis.

Said circumferential wall may have a shape of a circle, an ellipse, a square, a rectangle or a polygon.

Said circumferential wall may be made of translucent material. Said translucent material may be glass or quartz or acrylic plastic.

Said vessel may have a base for positioning said vessel on a ground and a top provided on the end opposite to the base when seen along said axis, and wherein the circumference of said circumferential wall may increase from said base towards said top. In various embodiments, such vessel may enable distribution of the light intensity within said vessel that increases from the base towards the top of the vessel along said axis so that the photoautotrophic organisms may receive an increasing distribution or portion of the light intensity as the photoautotrophic organisms, during the cultivation process, travel up said vessel from said base of the vessel towards said top of the vessel. Therefore, the portion of the light intensity distributed within said vessel increases from said base towards said top of said vessel such that the photoautotrophic organisms towards said top of said vessel may receive a higher proportion of the light intensity distributed within said vessel compared to the photoautotrophic organisms towards said base of said vessel.

Said device for providing an uneven distribution of the light intensity within said vessel along said axis may include at least one mirror positioned outside the vessel for directing light towards a predetermined area of said translucent circumferential wall or towards a predetermined translucent area of said circumferential wall so as to provide an uneven distribution of the light intensity within said vessel along said axis. In various embodiments, said mirror may enable distribution of the light intensity within the vessel that may increase from said base towards said top of said vessel along said axis so that the photoautotrophic organisms may receive an increasing distribution of the light intensity as the photoautotrophic organisms travel in a direction from said base of said vessel towards said top of said vessel during the cultivation process.

Said mirror may have a concave shape arranged to curve away from said circumferential wall of said vessel. Said mirror may be arranged to at least partially surround said circumferential wall of said vessel. Said mirror may be arranged to at least substantially surround said circumferential wall of said vessel.

Said device for providing an uneven distribution of the light intensity may include a light filtering layer on said circumferential wall of said vessel, wherein said light filtering layer may have a transmissivity to light that varies along said axis so as to provide an uneven distribution of the light intensity within said vessel along said axis.

Said device for providing an uneven distribution of the light intensity may include a filter arrangement positioned outside the vessel, wherein said filter arrangement may have a transmissivity to light that varies along said axis so as to provide an uneven distribution of the light intensity within said vessel along said axis.

Said device for providing an uneven distribution of the light intensity may include at least one light source positioned outside the vessel for supplying light towards a predetermined area of said translucent circumferential wall or towards a predetermined translucent area of said circumferential wall so as to provide an uneven distribution of the light intensity within said vessel along said axis.

Said device for providing an uneven distribution of the light intensity may include a plurality of light sources positioned outside the vessel for supplying light towards a plurality of predetermined areas of said translucent circumferential wall or towards a plurality of predetermined translucent areas of said circumferential wall, wherein said light sources may be spaced from said translucent circumferential wall or said circumferential wall of said vessel at respective distances that vary along said axis so as to provide an uneven distribution of the light intensity within said vessel along said axis.

Said device for providing an uneven distribution of the light intensity may include a plurality of light sources positioned outside the vessel for supplying light towards a plurality of predetermined areas of said translucent circumferential wall or towards a plurality of predetermined translucent areas of said circumferential wall, wherein the number of light sources for supplying light towards a respective predetermined area of said translucent circumferential wall or towards a respective predetermined translucent area of said circumferential wall, may vary along said axis so as to provide an uneven distribution of light intensity within said vessel along said axis.

Said bioreactor may further include one or more spaced apart dividers arranged to define a plurality of compartments within the vessel along said axis, wherein each divider may have at least one orifice defined through the divider for fluid communication between the plurality of compartments, and wherein, for each compartment, the light intensity within one compartment of the plurality of compartments may be different than the respective along said axis subsequent compartment of the plurality of compartments so as to provide an uneven distribution of the light intensity within said vessel along said axis. In various embodiments, the number of compartments may be between 2 and 15. Each compartment may correspond to a stage of the growth process of the photoautotrophic organisms.

In various embodiments, for each compartment, the height of one compartment of the plurality of compartments may be different than the respective along said axis subsequent compartment of the plurality of compartments. In various embodiments, for each compartment, the height of a compartment of the plurality of compartments may be smaller than the respective along said axis subsequent compartment of the plurality of compartments in the direction from said base towards said top.

In various embodiments, for each compartment, the distribution of the light intensity in a compartment may be smaller than that in a subsequent compartment in the direction from said base towards said top of said vessel.

Said orifice may have a diameter of between about 1 mm and about 10 mm.

Each divider may have a plurality of orifices, and wherein the spacing between two adjacent orifices may be between about 1 mm and about 10 mm.

Said bioreactor may further include a draft tube arranged in each compartment.

In various embodiments, for each compartment, the inner diameter of said draft tube may be different than that of the respective along said axis in subsequent compartment of the plurality of compartments. In various embodiments, for each compartment, the inner diameter of said draft tube may be smaller than the respective along said axis subsequent draft tube in the direction from said base towards said top.

Said light intensity may be between about 50 $\mu mol/m^2 s$ and about 1000 $\mu mol/m^2 s$.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1:
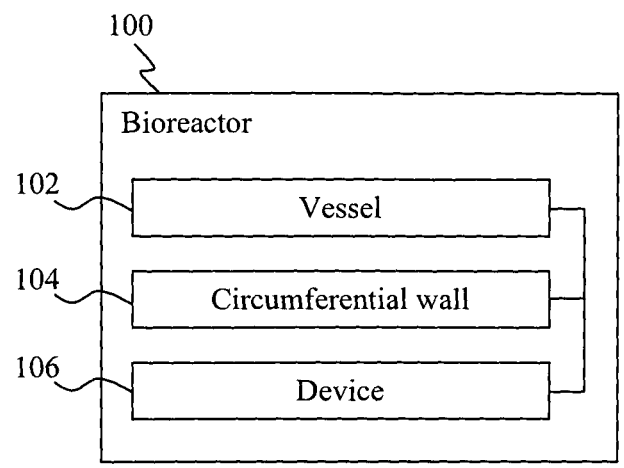
FIG. 1 shows a schematic block diagram of a bioreactor, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structura and logical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other method or device. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments.

Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element includes a reference to one or more of the features or elements.

In the context of various embodiments, the phrase "at least substantially" may include "exactly" and a reasonable variance. In the context of various embodiments, the term "about" or "approximately" as applied to a numeric value encompasses the exact value and a reasonable variance.

As used herein, the term "and/or" includes any and all combinations of one or more of the associated listed items.

Various embodiments relate to a bioreactor, for example a photobioreactor for growing photoautotrophic organisms (e.g. microalgae).

Cultivation of photoautotrophic organisms such as microalgae is generally carried out under constant light intensity. However, at the beginning of the cultivation period, the light intensity may be too high that the low concentration microalgae cells are placed under a state of photoinhibition, where the growth of the microalgae cells may become inhibited as a result of the high or saturated light intensity. On the other hand, the growth of microalgae to a moderately dense broth may cause light attenuation due to mutual shading. In this case, the microalgae cells in the zone or area which is away from the light source may be under a state of photolimitation due to insufficient light. In view of this, a lumostatic operation may be employed to improve the microalgae growth by optimizing the light energy supply to the microalgae cells during the growth process in order to reduce both photoinhibition and photolimitation. For the lumostatic approach, the distribution of the light intensity acting on the photoautotrophic organisms may be varied during the cultivation process of the photoautotrophic organisms, corresponding to the growth stage of the photoautotrophic organisms.

Various embodiments may therefore provide bioreactors, including their designs, for the cultivation of photoautotrophic organisms and methods for cultivating photoautotrophic organisms, based on the approach of lumostatic cultivation for achieving continuous production of photoautotrophic organisms.

FIG. 1 shows a schematic block diagram of a bioreactor 100 for growing photoautotrophic organisms, according to various embodiments. The bioreactor 100 includes a vessel 102 configured to receive the photoautotrophic organisms, the vessel 102 having a longitudinal axis, which a circumferential wall 104 extends around the longitudinal axis, wherein the circumferential wall 104 is translucent so as to enable light to enter the vessel 102 from the outside for acting on the photoautotrophic organisms, wherein a device 106 for providing an uneven distribution of the light intensity within the vessel 102 along the longitudinal axis is provided.

In other words, the bioreactor 100 may have an elongate vessel 102 having a circumferential wall 104 that extends longitudinally. The circumferential wall 104 may be at least translucent, in other words having a degree of transmissivity to light, to allow external light to enter through the circumferential wall 104 into the interior of the vessel 102. The vessel 102 may receive the photoautotrophic organisms to be cultivated and the light passing into the vessel 102 may act or impinge on the photoautotrophic organisms to aid the cultivation process.

The bioreactor 100 may also include a device 106 for providing an uneven distribution of the light intensity within the vessel 102 along the longitudinal axis. The light intensity may be unevenly distributed within the vessel 102 along the longitudinal axis of the vessel 102 so that the photoautotrophic organisms may receive different distributions of the light intensity at different stages or compartments of the vessel 102 as the photoautotrophic organisms travel within the vessel 102 in a direction at least substantially along the longitudinal axis during the cultivation process. For example, the vessel 102 is an upstanding vessel and the photoautotrophic organisms may progress from the base of the vessel 102 to the top of the vessel 102 during the cultivation process, and the portion of the light intensity distributed within the vessel 102 may increase from the base to the top of the vessel 102, along the longitudinal axis. This means that the photoautotrophic organisms towards the top of the vessel 102 may receive a higher proportion of the light intensity distributed within the vessel 102 compared to the photoautotrophic organisms towards the base of the vessel 102. This provides a lumostatic cultivation approach that may provide a respective optimum distribution of the light intensity corresponding to the respective growth stage of the photoautotrophic organisms during the cultivation process within the vessel 102.

In the context of various embodiments, the vessel 102 may also be referred to as a chamber or a core structure or a column structure.

In the context of various embodiments, the circumferential wall 104 may have a shape of a circle, an ellipse, a square, a rectangle or a hexagon. However, it should be appreciated that other polygonal shapes may be provided.

In the context of various embodiments, the device 106 for providing an uneven distribution of the light intensity includes the circumferential wall 104 such that the translucent surface varies along the longitudinal axis of the vessel 102. In other words, variation in the translucent surface of the circumferential wall 104 along the longitudinal axis may result in the uneven distribution of the light intensity within the vessel 102. As non-limiting examples, the variation in the translucent surface may be in terms of the dimensions of the translucent surface area that may be exposed to light to allow external light to enter the vessel 102 and/or the degree of transmissivity of the translucent surface to light. In one embodiment, the circumference of the circumferential wall 104 may vary along the longitudinal axis, such that the translucent surface varies along the longitudinal axis of the vessel 102.

In the context of various embodiments, the circumferential wall 104 is made of a translucent material. In various embodiments, the entire circumferential wall 104 may be at least substantially translucent so as to allow light to enter the vessel 102 through any portion or predetermined area of the translucent circumferential wall 104. In various embodiments, at least a portion of the circumferential wall 104 may be translucent so as to provide a translucent area to allow light to enter the vessel 102 through a predetermined translucent area of the circumferential wall 104. Furthermore, it should be appreciated that a non-translucent frame or support structure may be provided for holding or securing the circumferential wall 104. The frame may form part of the circumferential wall 104 and light may therefore enter the vessel 102 through a predetermined translucent area of the circumferential wall 104, in other words through a portion of the circumferential wall 104 other than the frame. However, it should be appreciated that the frame may also be translucent so as to permit a degree of light to pass through.

In the context of various embodiments, the circumferential wall 104 may be transparent. In the context of various embodiments, the translucent material or the transparent material may include but not limited to glass, quartz and acrylic plastic. The translucent material or the transparent material may allow direct exposure to sunlight to pass through to act on the photoautotrophic organisms.

In the context of various embodiments, the vessel 102 has a base for positioning the vessel 102 on a ground or a surface and a top provided on the end opposite to the base when seen along the longitudinal axis, and wherein the circumference of the circumferential wall 104 may increase from the base towards the top. In other words, the vessel 102 may be an upstanding vessel with a tapering cross section adapted to flare (e.g. taper outwardly) in the direction from the base towards the top of the vessel 102 along the longitudinal axis. Therefore, the vessel 102 may have a shape resembling a reverse conical shape. The increase in the circumference of the circumferential wall 104 from the base towards the top may be continuous or continual, for example the vessel 102 may include at least one portion of the circumferential wall 104 having a uniform circumference.

In various embodiments, the vessel 102 having the tapering configuration may enable distribution of the light intensity within the vessel 102 that increases from the base towards the top of the vessel 102 along the longitudinal axis so that the photoautotrophic organisms may receive an increasing distribution or portion of the light intensity as the photoautotrophic organisms, during the cultivation process, travel up the vessel 102 from the base of the vessel 102 towards the top of the vessel 102. This means that the portion of the light intensity distributed within the vessel 102 increases from the base towards the top of the vessel 102 such that the photoautotrophic organisms towards the top of the vessel 102 may receive a higher proportion of the light intensity distributed within the vessel 102 compared to the photoautotrophic organisms towards the base of the vessel 102. This may provide a lumostatic cultivation approach that may provide a respective optimum distribution of the light intensity corresponding to the respective growth stage of the photoautotrophic organisms during the cultivation process within the vessel 102. In addition, the vessel 102 having such a taper configuration may also allow, at the top of the vessel 102, a larger proportion of light to enter the vessel.

In the context of various embodiments of the vessel 102 having a taper configuration, the ratio of the diameter (or cross sectional width) of the top of the vessel 102 to the diameter (or cross sectional width) of the base of the vessel may be about 5 to 1.

In the context of various embodiments, the device 106 may include at least one mirror positioned outside the vessel 102 for directing light towards a predetermined area of the translucent circumferential wall 104 or towards a predetermined translucent area of the circumferential wall 104 so as to provide an uneven distribution of the light intensity within the vessel along the longitudinal axis. The mirror may be arranged to at least partially surround the circumferential wall 104 of the vessel 102, for example arranged on one or more sides of the vessel 102 or at least substantially surrounding the vessel 102. In various embodiments, the mirror may enable distribution of the light intensity within the vessel 102 that increases from the base towards the top of the vessel 102 along the longitudinal axis so that the photoautotrophic organisms may receive an increasing distribution of the light intensity as the photoautotrophic organisms travel in a direction from the base of the vessel 102 towards the top of the vessel 102 during the cultivation process.

In various embodiments, the mirror may have a concave shape arranged to curve away from the circumferential wall 104 of the vessel 102. This may focus the light incident on the mirror towards the vessel 102, thereby concentrating the light towards a predetermined area of the translucent circumferential wall 104 or towards a predetermined translucent area of the circumferential wall 104, rather than spread over a larger area of the translucent circumferential wall 104 or the translucent area of the circumferential wall 104.

In the context of various embodiments, the device 106 may include a light filtering layer on the circumferential wall 104 of the vessel 102, wherein the light filtering layer has a transmissivity to light that varies along the longitudinal axis so as to provide an uneven distribution of the light intensity within the vessel 102 along the axis.

In various embodiments, the degree of transmissivity to light of the light filtering layer may increase from the base towards the top of the vessel 102 along the longitudinal axis of the vessel 102. Therefore, in various embodiments, the light filtering layer may enable distribution of the light intensity within the vessel 102 that increases from the base towards the top of the vessel 102 along the longitudinal axis so that the photoautotrophic organisms may receive an increasing distribution of the light intensity as the photoautotrophic organisms travel in a direction from the base of the vessel 102 towards the top of the vessel 102 during the cultivation process.

In the context of various embodiments, the light filtering layer may be provided, at least partially, on an outer surface and/or an inner surface of the circumferential wall 104, for example in the form of a coating. The light filtering layer may be a single layer with a varying degree of transmissivity to light or may include a plurality of layers to provide various degrees of transmissivity to light at different portions of the light filtering layer.

In the context of various embodiments, the device 106 may include a filter arrangement positioned outside the vessel 102, wherein the filter arrangement has a transmissivity to light that varies along the longitudinal axis so as to provide an uneven distribution of the light intensity within the vessel 102 along the axis.

In various embodiments, the degree of transmissivity to light of the filter arrangement may increase from the base towards the top of the vessel 102 along the longitudinal axis of the vessel 102. Therefore, in various embodiments, the filter arrangement may enable distribution of the light intensity within the vessel 102 that increases from the base towards the top of the vessel 102 along the longitudinal axis so that the photoautotrophic organisms may receive an increasing distribution of the light intensity as the photoautotrophic organisms travel in a direction from the base of the vessel 102 towards the top of the vessel 102 during the cultivation process.

In the context of various embodiments, the filter arrangement may be arranged to at least partially surround the circumferential wall 104 of the vessel 102, for example arranged on one or more sides of the vessel 102 or at least substantially surrounding the vessel 102. The filter arrangement may be a single filter with a varying degree of transmissivity to light or may include a plurality of filters to provide various degrees of transmissivity to light at different portions of the filter arrangement.

In the context of various embodiments, the device 106 may include at least one light source positioned outside the vessel 102 for supplying light towards a predetermined area of the translucent circumferential wall 104 or towards a predetermined translucent area of the circumferential wall 104 so as to provide an uneven distribution of the light intensity within the vessel 102 along the longitudinal axis. The light source may supply light towards one or more sides of the vessel 102.

In various embodiments, the light source may be adapted and/or arranged to supply light such that the distribution of the light intensity within the vessel 102 increases from the base towards the top of the vessel 102 along the longitudinal axis so that the photoautotrophic organisms may receive an increasing distribution of the light intensity as the photoautotrophic organisms travel in a direction from the base of the vessel 102 towards the top of the vessel 102 during the cultivation process. As a non-limiting example, the light source may include a filter having a varying degree of transmissivity to light so as to provide an uneven distribution of the light intensity within the vessel 102 along the longitudinal axis. As a further non-limiting example, the light source, for example having an elongate form, may be arranged along one or more sides of the vessel 102 at a distance relative to the circumferential wall 104 of the vessel that decreases from the base towards the top of the vessel 102.

In the context of various embodiments, the device 106 may include a plurality of light sources positioned outside the vessel 102 for supplying light towards a plurality of predetermined areas of the translucent circumferential wall 104 or towards a plurality of predetermined translucent areas of the circumferential wall 104, wherein the light sources may be spaced from the translucent circumferential wall 104 or the circumferential wall 104 of the vessel 102 at respective distances that vary along the longitudinal axis so as to provide an uneven distribution of the light intensity within the vessel 102 along the axis. The plurality of light sources may supply light towards one or more sides of the vessel 102.

In various embodiments, the plurality of light sources may be arranged at a distance relative to the circumferential wall 104 of the vessel that decreases from the base towards the top of the vessel 102 so that the photoautotrophic organisms may receive an increasing distribution of the light intensity as the photoautotrophic organisms travel in a direction from the base of the vessel 102 towards the top of the vessel 102 during the cultivation process.

In the context of various embodiments, the device 106 may include a plurality of light sources positioned outside the vessel 102 for supplying light towards a plurality of predetermined areas of the translucent circumferential wall 104 or towards a plurality of predetermined translucent areas of the circumferential wall 104, wherein the number of light sources for supplying light towards a respective predetermined area of the translucent circumferential wall 104 or towards a respective predetermined translucent area of the circumferential wall 104, varies along the longitudinal axis so as to provide an uneven distribution of light intensity within the vessel 102 along the longitudinal axis. The plurality of light sources may supply light towards one or more sides of the vessel 102.

In various embodiments, the number of light sources per predetermined area or predetermined translucent area increases from the base towards the top of the vessel 102 along the longitudinal axis so that the photoautotrophic organisms may receive an increasing distribution of the light intensity as the photoautotrophic organisms travel in a direction from the base of the vessel 102 towards the top of the vessel 102 during the cultivation process.

In the context of various embodiments, the bioreactor 100 may further include one or more spaced apart dividers arranged to define a plurality of compartments within the vessel 102 along the longitudinal axis, wherein each divider has at least one orifice defined through the divider for fluid communication between the plurality of compartments, and wherein, for each compartment, the distribution of the light intensity within one compartment of the plurality of compartments is different than the respective along the longitudinal axis subsequent compartment of the plurality of compartments so as to provide an uneven distribution of the light intensity within the vessel 102 along the axis. Therefore, the bioreactor 100 may have a multi-compartment configuration.

In various embodiments, the number of compartments may be between 2 and 15, for example between 2 and 10, between 2 and 4, between 4 and 15 or between 4 and 8. Each compartment may correspond to a stage of the growth process of the photoautotrophic organisms.

In various embodiments, the height of one compartment of the plurality of compartments may be different than the respective along the longitudinal axis subsequent compartment of the plurality of compartments so that the distribution of the light intensity for each compartment may be different. For example, for each compartment, the height of a compartment may be smaller than the height of a respective subsequent compartment in the direction from the base towards the top of the vessel 102.

In various embodiments, in addition to or alternative to the height of the compartment, the translucent surface of the circumferential wall 104 and/or the circumference of the circumferential wall 104 corresponding to one compartment of the plurality of compartments may be different than the respective along the longitudinal axis subsequent compartment of the plurality of compartments so that the distribution of the light intensity for each compartment may be different. Furthermore, additionally or alternatively, the light filtering layer and/or the filter arrangement corresponding to different compartments may have different transmissitivities to light, and/or the light source(s) may be adapted to supply light such that the distribution of the light intensity for each compartment is different.

In the context of various embodiments, for each compartment, the distribution of the light intensity in a compartment may be smaller than that in a subsequent compartment in the direction from the base towards the top of the vessel 102.

In various embodiments, each divider may extend through the circumferential wall 104 of the vessel 102. In one example of such an arrangement, the vessel 102 may be assembled from separate circumferential walls 104 corresponding to respective compartments, that are stacked one over the other with a divider in between adjacent compartments.

In various embodiments, each divider may be attached within the vessel 102 to an inner side wall of the circumferential wall 104. In such an arrangement, the vessel 102 may be a continuous structure having a continuous circumferential wall 104.

In the context of various embodiments, each or the orifice of each divider may have a diameter of between about 1 mm and about 10 mm, for example between about 1 mm and about 5 mm, between about 1 mm and about 3 mm, between about 5 mm and about 10 mm or between about 2 mm and about 5 mm. The orifice may be arranged centrally of each divider.

In the context of various embodiments, each divider may have a plurality of orifices, and wherein the spacing or pitch between two adjacent orifices e.g. between the respective centre points of adjacent orifices, is between about 1 mm and about 10 mm, for example between about 1 mm and about 5 mm, between about 1 mm and about 3 mm, between about 5 mm and about 10 mm or between about 2 mm and about 5 mm.

In the context of various embodiments, each divider may function as a gas-liquid distributor to distribute and disperse the gas supplied to the interior of the vessel 102, and/or to aid generation of gas bubbles for distribution of the gas.

In the context of various embodiments, the bioreactor 100 may further include a draft tube arranged in each compartment. The draft tube may aid the circulation of the photoautotrophic organisms within the compartment and/or to the subsequent compartment, during the cultivation process.

In various embodiments, for each compartment, the inner diameter of the draft tube is different than that of the respective along the longitudinal axis in subsequent compartment of the plurality of compartments. For example, for each compartment, the inner diameter of the draft tube in a compartment may be smaller than the inner diameter of the draft tube in a respective subsequent compartment in the direction from the base towards the top of the vessel 102. The draft tubes may be concentric draft tubes and each draft tube may be at least substantially aligned with the orifice(s) of each divider so that the liquid medium and the gas supplied to the interior of the vessel 102 may be distributed to the core of the draft tube within the circumferential wall of the draft tube and/or the annular region of the draft tube, exterior to the circumferential wall of the draft tube.

Each draft tube may have a different cross sectional width or diameter and/or height, depending on the diameter/circumference of the circumferential wall corresponding to the compartment and/or the height of the compartment in which the respective draft tube is positioned. In various embodiments, the ratio of the diameter of the draft tube to the diameter of the circumferential wall of the vessel 102 (or the ratio of the draft tube cross sectional area to the vessel cross sectional area) defining the compartment corresponding to the draft tube may be between 0.1 and 0.9, for example between 0.1 and 0.7, between 0.1 and 0.5, between 0.5 and 0.9, or between 0.3 and 0.7. It should be appreciated that each draft tube may have any suitable diameter, with the ratio of the diameter of the draft tube to the diameter of the circumferential wall of the vessel 102 being at least substantially within any of the above-mentioned ranges. In addition, it should be appreciated that each draft tube may have any suitable height. In various embodiments, each draft tube may be constructed by any material, including for example a transparent material or an opaque material.

In the context of various embodiments, light intensity may be between about 50 $\mu mol/m^2 s$ and about 1000 $\mu mol/m^2 s$, for example between about 50 $\mu mol/m^2 s$ and about 600 $\mu mol/m^2 s$, between about 50 $\mu mol/m^2 s$ and about 400 $\mu mol/m^2 s$, between about 200 $\mu mol/m^2 s$ and about 1000 $\mu mol/m^2 s$ or between about 100 $\mu mol/m^2 s$ and about 600 $\mu mol/m^2 s$.

In the context of various embodiments, fresh liquid medium (e.g. culture medium) containing photoautotrophic organisms for cultivation, and a mixture of air and carbon dioxide gas may be supplied to the vessel 102 through the base of the vessel 102. The liquid and gas may pass through the dividers, each acting as a gas-liquid distributor, substantially simultaneously. The gas may be present in the form of bubbles in the liquid. The bubbles may progress towards the top of the vessel 102 and the rising bubbles may flow through the hollow core or interior of the draft tube, thereby inducing internal circulation of the liquid and photoautotrophic organisms in the liquid through the core of the draft tube, outwardly from the top of the draft tube and also inwardly into the interior of the draft tube from the bottom of the draft tube.

In various embodiments, each draft tube may impede light penetration into the interior of the draft tube, and therefore photoautotrophic organisms at the annular region, at spaces between the circumferential wall 104 of the vessel 102 and the circumferential wall of the draft tube, may receive a higher proportion of the light intensity. It should be appreciated that each draft tube may be made of a translucent material or a transparent material that may allow a higher degree of light penetration into the interior of the draft tube. In any case, the degree of light penetration also depends on the microalgae concentration. As the microalgae grows and multiplies, the light penetration decreases. Accordingly, as the growth process progresses, light penetration into the interior of the vessel 102 and also the interior of the draft tube may be progressively impeded.

In various embodiments, as the top of the vessel 102 may also allow light to enter the vessel 102, the liquid medium at the top of the vessel 102, at least to a certain depth from the surface of the liquid medium, may also be exposed to light. For example, sunlight may enter the vessel 102 through the top of the vessel 102 where the cultivation process is performed outdoors.

In the context of various embodiments, the photoautotrophic organisms may be microalgae, for example of a species including but not limited to *Chlorella* sp., *Synechoccus* PC 6301, *Haematococcus pluvialis*, *Anabaena variabilis*, or *Neochloris oleoabundan*.

In order that the invention may be readily understood and put into practical effect, particular embodiments will now be described by way of examples and not limitations, and with reference to the figures.

Figure 2:
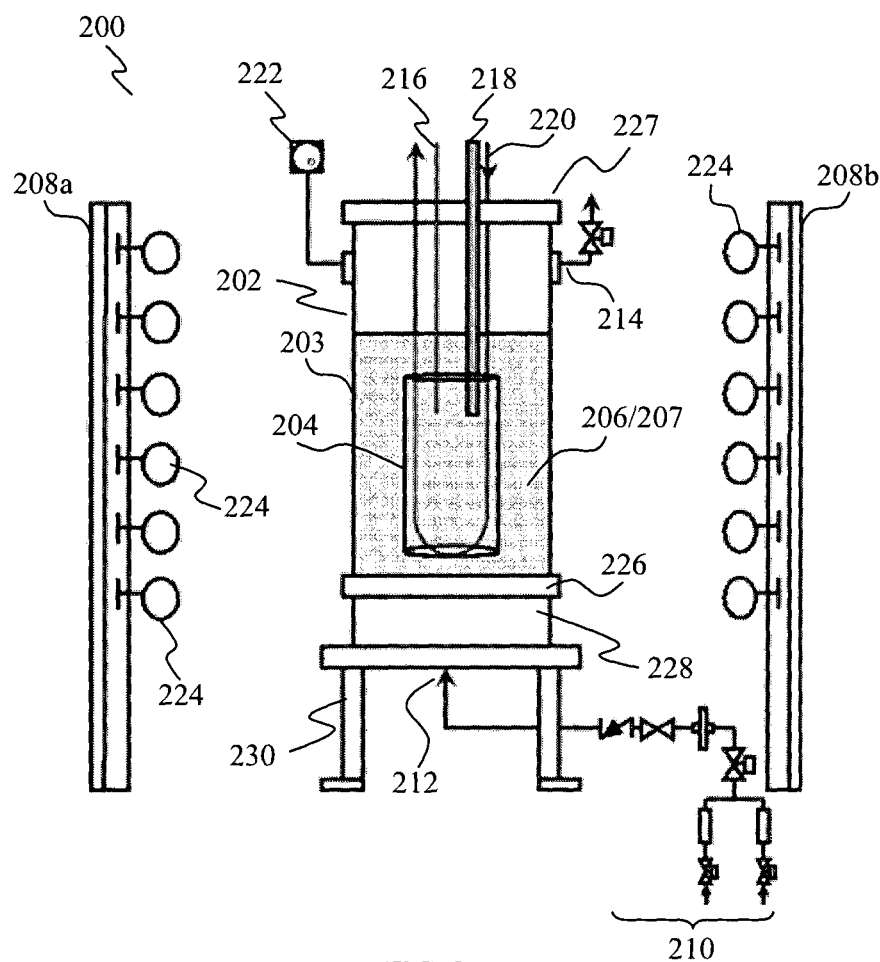
FIG. 2 shows a schematic diagram of a bioreactor, according to various embodiments.

FIG. 2 shows a schematic diagram of a bioreactor 200 for growing photoautotrophic organisms, according to various embodiments. The bioreactor 200 includes a vessel or main column 202 having a circumferential wall 203 extending longitudinally. The vessel 202 may have a circular cross section. The vessel 202 has a top 227 and a base 228. The base 228 may be positioned on a support structure 230 having legs for positioning the vessel 202 on a ground or a surface, with the base 228 elevated. The support structure 230 may be integral to the base 228 or may be a separate structure.

The bioreactor 200 includes a draft tube 204 arranged within the vessel 202. The photoautotrophic organisms (e.g. microalgae) 206 for cultivation are contained within the vessel 202. The microalgae 206 may be provided or suspended in a liquid (e.g. a culture medium) 207.

The bioreactor 200 further includes light sources in the form of two light panels 208a, 208b, a gas source for supplying gas to the vessel 202 through the base 228 of the vessel 202, via a valve arrangement 210 and a gas inlet 212, a gas outlet 214 positioned towards the top 227 of the vessel 202 from which gas may be removed from the vessel 202, a temperature controller (e.g. Polyscience, Ill., USA) having a thermocouple 216, a dissolved oxygen ($O_2$) probe 218, a piping or conduit 220 for supplying cooling water, and a pressure indicator or gauge 222.

The two light panels 208a, 208b, may be arranged on opposite sides of the vessel 202, to provide light to the microalgae 206 contained within the vessel 202. Each light panel 208a, 208b, may include a plurality of light bulbs 224, for example 30 fluorescence bulbs (e.g. Philips 8 W). However, it should be appreciated that any number of light bulbs 224 and/or any arrangement of the light panels 208a, 208b on any side(s) of the vessel 202 may be provided, for example depending on the cultivation requirements.

The vessel 202 may be made of substantially translucent or transparent material. In one embodiment, the vessel 202 may be made of transparent acrylic plastic. The vessel 202 may have a uniform inner diameter of about 100 mm and a height of about 300 mm, with a working volume of approximately 1500 mL. The draft tube 204 may have a diameter of about 74 mm and may be arranged about 35 mm above a gas distributor 226 to ensure effective circulation of the liquid 207 containing the microalgae 206. The gas distributor 226 may be a perforated plate having a plurality of orifices, with an orifice diameter of about 1 mm and a pitch distance of about 5 mm. Samples of the microalgae, after cultivation, may be collected from a sampling port (not shown) located at about 32.5 mm above the gas distributor 226. The conditions of the culture of microalgae 206 may be monitored via one or more of the thermocouple 216, the dissolved oxygen probe 218, the pressure gauge 222 and a pH probe (not shown).

The gas supplied to the vessel 202 may be a mixture of compressed air and compressed carbon dioxide ($CO_2$), which is flowed upstream of the vessel 202 from the gas inlet 212 towards the gas outlet 214.

During cultivation of the microalgae using the bioreactor 200, the concentration of $CO_2$ may be about 2% (v/v), and a total flow rate of the gas supplied to the vessel 202 may be approximately 0.26 vvm (volume of gas per volume of liquid medium per minute). A substantially constant culture temperature of about 28° C. may be maintained throughout the cultivation period.

During the growth period, the light intensity provided to the microalgae 206 may be controlled or varied, for example, by supplying light of a lower intensity at the early stage of microalgae cultivation, and light of a higher intensity at the later stage of the cultivation, to minimize the photoinhibition and photolimitation effects. Results show that such an approach may increase the microalgae productivity by about 74.3% as compared to the conventional operating condition using a constant light intensity.

In various embodiments, during the growth of the microalgae 206, the light intensity within the interior of the vessel 202 may be varied by controlling the number of the light bulbs 224 supplying light to the interior of the vessel 202 and to the microalgae 206 (e.g. by switching on a selected number of light bulbs 224 corresponding to the required light intensity) and/or controlling the distance between one or both light panels 208a, 208b, relative to the circumferential wall 203.

In lumostatic cultivation, an increase in light exposure over the growth period of the photoautotrophic organism is provided. In various embodiments, bioreactors for lumostatic cultivation of photoautotrophic organisms may be designed taking into consideration that photoautotrophic organisms cultivated in the bioreactor are located towards the base of the bioreactor vessel during the early stages of the cultivation or growth process, and that as the growth process progresses, the photoautotrophic organisms travel upstream or upwards towards the top of the vessel. As such, for the design of the bioreactor of various embodiments, the light exposure or distribution of light intensity may be increased in the upward direction from the base towards the top of the vessel, which fits well with the growth period or process of the photoautotrophic organisms, in embodiments where the photoautotrophic organisms move from the base to the top of the vessel.

Therefore, an upstanding bioreactor vessel may be constructed or designed such that the photoautotrophic organisms towards the bottom of the vessel, during the earliest growth stage, may receive a low distribution of light intensity, or at least a lower distribution as compared to that received at subsequent stages of the vessel towards the top of the vessel. Furthermore, the upstanding bioreactor vessel may be designed such that as the photoautotrophic organisms travel upstream through portions or stages of the vessel during different growth stages towards the top of the vessel, the distribution of the light intensity acting on the photoautotrophic organisms increases. Therefore, the vessel may be designed such that the distribution of the light intensity within the vessel is the highest at the top of the vessel for the final cultivation stage of the photoautotrophic organisms.

In various embodiments, the distribution of the light intensity within the vessel at respective different portions or stages of the vessel of the bioreactor along a longitudinal axis of the vessel may be pre-determined based on the protocol or strategy to be employed for the cultivation process in order to achieve maximum or optimum production of the photoautotrophic organisms.

Figure 3:
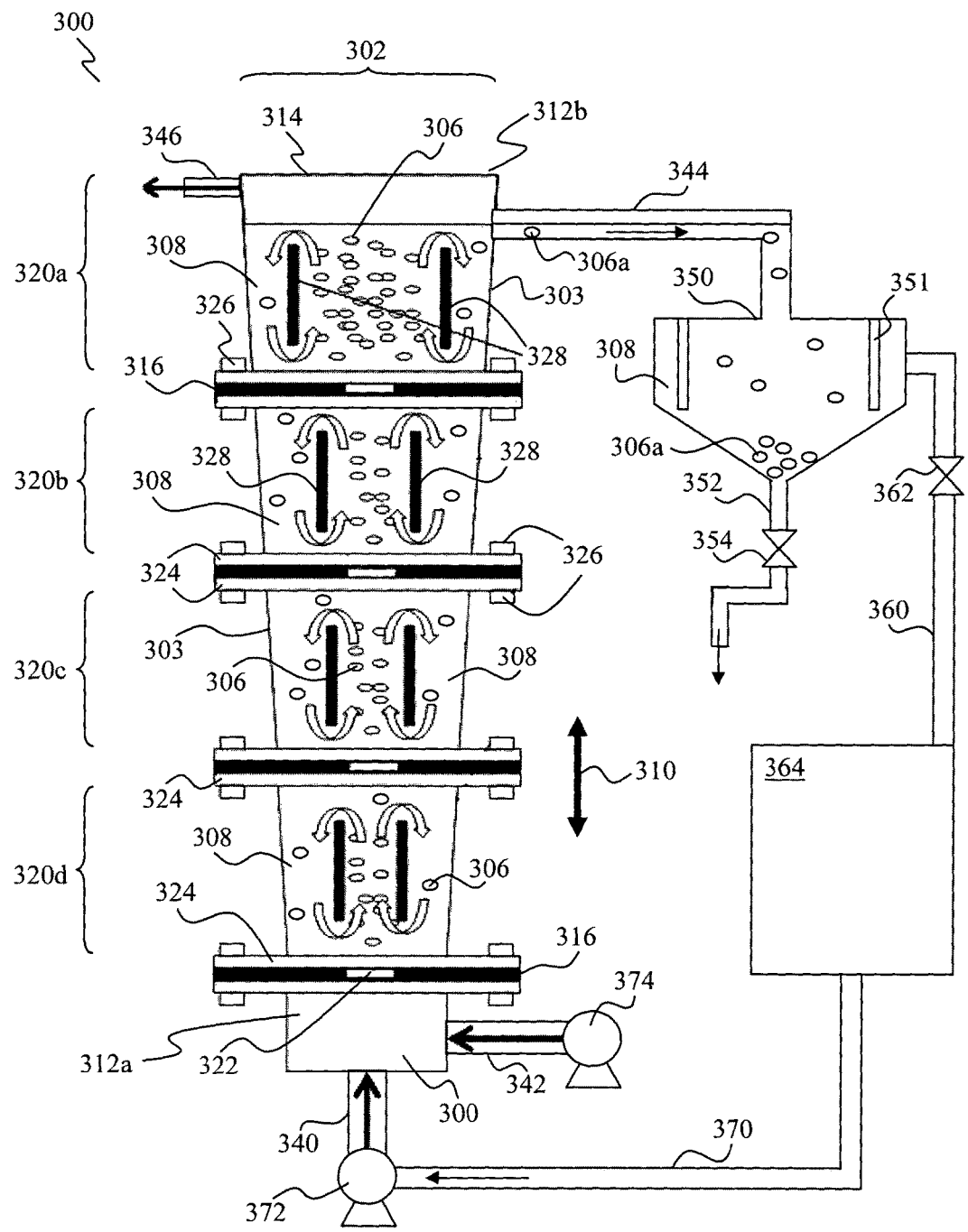
FIG. 3 shows a schematic diagram of a bioreactor, according to various embodiments.

FIG. 3 shows a schematic diagram of a bioreactor 300 for growing photoautotrophic organisms, according to various embodiments. The bioreactor 300 includes a vessel or main column 302 having a longitudinal axis, as represented by the double-headed arrow 310, which a circumferential wall 303 extends around the longitudinal axis 310. The vessel 302 may have a circular cross section. The vessel 302 has a base 312a and a top 312b. The photoautotrophic organisms (e.g. microalgae) 306 for cultivation, provided or suspended in a liquid (e.g. a culture medium) 308, are contained within the vessel 302. The vessel 302 may be made of one or more transparent acrylic sheets.

At least a portion of the vessel 302 has a tapering cross section adapted to flare (e.g. taper outwardly) in a direction along the longitudinal axis 310 of the vessel 302, from the base 312a towards the top 312b of the vessel 302. In other words, the vessel 302 has a cross-sectional width or diameter that decreases towards the base 312a, and increases towards the top 312b.

In this configuration, the circumferential wall 303 has a circumference of a smaller dimension towards the base 312a, and which the circumference increases towards the top 312b of the vessel 302. Therefore, the photoautotrophic organisms 306 located towards the base 312a of the vessel 302, during the initial growth period, may receive a lower distribution of light intensity due to the smaller surface area, as a result of a smaller circumference, available for exposure to a light signal (e.g. from solar radiation or artificial light source(s)). As the circumference of the tapering vessel 302 increases towards the top 312b, the photoautotrophic organisms 306, during the intermediate growth periods, may receive an increasing distribution of the light intensity as the photoautotrophic organisms 306 travel upstream towards the top 312b during the different cultivation stages, such that the photoautotrophic organisms 306 located towards the top 312b, during the final growth period, may be provided with the highest distribution of the light intensity for the final cultivation stage. In addition, the surface 314 of the top 312b may be exposed to a light signal (e.g. incoming solar light), such that the photoautotrophic organisms 306 located towards the top 312b may be exposed to additional light signal through the top 312b.

In the embodiment as shown in FIG. 3, the vessel 302 has a continuously tapering cross section. However, it should be appreciated that the tapering cross section portion of the vessel 302 may include one or more portions having a uniform cross-section dimension at intervals along the tapering cross section portion of the vessel 302 such that the vessel 302 has a continually tapering cross section.

The vessel 302 is provided with a number of gas-liquid distributors 316 along the length of the vessel 302. The gas-liquid distributors 316 are spaced apart and act as dividers to define a plurality of compartments 320a, 320b, 320c, 320d, within the vessel 302 along the longitudinal axis 310.

Each gas-liquid distributor (e.g. a perforated plate) 316 includes one or more orifices, collectively shown as 322, defined through the gas-liquid distributor 316 to allow the liquid 308 and the gas to be supplied to the liquid 308 to flow between different compartments 320a, 320b, 320c, 320d, thereby allowing fluid communication between the plurality of compartments 320a, 320b, 320c, 320d. Each gas-liquid distributor 316 also assists in distributing and dispersing the gas into the interior of each compartment 320a, 320b, 320c, 320d. Each gas-liquid distributor 316 may have a thickness of about 10 mm, but not so limited. Each gas-liquid distributor 316 may be as described later in the context of the embodiment shown in FIG. 4C.

Each gas-liquid distributor 316 may be held between two flanges 324 extending from the circumferential wall 331 of the vessel 302, where the gas-liquid distributor 316 and the two flanges 324 are secured together by securing means (e.g. bolts) 326 to hold and secure the gas-liquid distributor 316. The two flanges 324 may lie around the peripheral edges of the gas-liquid distributor 316, respectively on the top and bottom faces of the gas-liquid distributor 316. Each flange 324 may have a thickness of about 10 mm, but not so limited.

In various embodiments, in order to construct the vessel 302, respective circumferential walls corresponding to the respective compartments 320a, 320b, 320c, 320d may be arranged or assembled one over the other, and aligned relative to each other. For example, separate circumferential walls corresponding to the respective compartments 320a, 320b, 320c, 320d may be provided. The circumferential wall corresponding to the compartment 320c may then be stacked or arranged over the circumferential wall corresponding to the compartment 320d, and sandwiching a gas-liquid distributor 316 in between, which may be secured together with the flanges 324 associated with the circumferential walls corresponding to the compartments 320c, 320d. One or more further circumferential walls may be arranged over the compartments 302c, 302d to form additional compartments, e.g. compartment 302b, followed by compartment 302a.

However, it should be appreciated that other constructions or arrangements may be possible. As a non-limiting example, a single vessel structure may be provided, with one or more dividers or gas-liquid distributors being arranged in the interior of the vessel structure to define a plurality of compartments.

A respective draft tube (as shown in a cross-sectional view for clarity purposes) 328 may be provided in each compartment 320a, 320b, 320c, 320d. Each draft tube 328 may have a circular cross section. For each compartment 320a, 320b, 320c, 320d, the inner diameter of the draft tube 328 is smaller than the inner diameter of the respective draft tube 328 in subsequent compartment of the plurality of compartments 320a, 320b, 320c, 320d in the direction from the base 312a towards the top 312b. In other words, increasingly larger diameter draft tubes 328 are arranged in the direction from the base 312a towards the top 312b. Each draft tube 328 may have its hollow core at least substantially aligned with the orifice(s) 322 so as to distribute the supplied gas to the hollow core in order to circulate the photoautotrophic organisms 306 through the hollow core of the draft tube 328, as well as in and out of the hollow core, for example as illustrated by the block arrows shown in each compartment 320a, 320b, 320c, 320d. The draft tubes 328 may be concentric, or in other words, arranged in a concentric configuration. The draft tubes 328 may be attached to support structures (not shown) that are in turn attached or fixed to the inner side wall of the vessel 302. The ratio of the diameter of a draft tube provided in a respective compartment 320a, 320b, 320c, 320d, to the diameter of the circumferential wall corresponding to the respective compartment 320a, 320b, 320c, 320d, may be between 0.1 and 0.9, for example between 0.1 and 0.7, between 0.1 and 0.5, between 0.5 and 0.9, or between 0.3 and 0.7.

The vessel 302 may include a liquid inlet 340 through which the photoautotrophic organisms 306 and the liquid 308 may be supplied to the interior of the vessel 302 for cultivation, and a gas inlet 342 through which a gas may be supplied to the interior of the vessel 302.

The vessel 302 may further include a liquid outlet 344 through which a portion of the liquid 308, including the photoautotrophic organisms 306a, after cultivation, may be removed from the vessel 302, and a gas outlet 346 through which a portion of the gas supplied to the interior of the vessel 302 and/or gas produced by the photoautotrophic organisms 306 during cultivation, may be removed.

The cultivated photoautotrophic organisms 306a may be provided to a tank 350. A cylindrical divider (as shown in a cross-sectional view for clarity purposes) 351 may be provided in the tank 350, extending from the top of the tank 350 towards the bottom of the tank 350, such that the photoautotrophic organisms 306a that may be entrained through the conduit 360 with a coupled valve 362 may be minimized. The cultivated photoautotrophic organisms 306a may settle in the tank 350, and subsequently at least a portion of the cultivated photoautotrophic organisms 306a may be removed from the tank 350 via a conduit 352 with a coupled valve 354 to provide a concentrated biomass (e.g. algal biomass).

A portion of the liquid 308 in the tank 350 may be removed and fed, via the conduit 360 with the coupled valve 362, to a medium feed tank 364, to be re-supplied to the vessel 302. The medium feed tank 364 includes a culture of the photoautotrophic organisms 306 to be grown and cultivated, which may be supplied via a conduit 370 to a liquid pump 372 to be pumped into the vessel 302 via the liquid inlet 340. The liquid pump 372 may provide the culture, including the liquid 308 and the photoautotrophic organisms 306, at a rate of about 6 L/hour, as a non-limiting example. It should be appreciated that other flow rates may be used.

The bioreactor 300 further includes a gas compressor 374 to supply gas to the vessel 302 via the gas inlet 342. The gas compressor 374 may supply the gas at a rate of about 200 L/min, as a non-limiting example. It should be appreciated that other flow rates may be used. The gas may be a mixture of compressed air and compressed carbon dioxide ($CO_2$). The gas may be present in the form of bubbles in the vessel which may aid circulation of the photoautotrophic organisms 306. The gas-liquid distributor 316 may assist in distributing or dispersing the bubbles as the gas passes through the gas-liquid distributor 316.

While FIG. 3 shows a 4-compartment or 4-stage bioreactor 300, it should be appreciated that any number of compartments or stages may be provided in the vessel 302.

While two inlets 340, 342 are shown in FIG. 3, it should be appreciated that a single common inlet, with a suitable valve arrangement, may be provided through which the liquid and gas may be supplied to the interior of the vessel 302. Similarly, a single common inlet, with a suitable valve arrangement, may be provided through which the liquid and gas may be removed from the interior of the vessel 302.

While not shown, it should be appreciated that monitoring devices, including but not limited to a temperature controller, a dissolved oxygen ($O_2$) probe, a pH probe, a pressure gauge and a light sensor, may be provided in the bioreactor 300 for monitoring the cultivation conditions.

The cultivation process may be carried out based on a similar approach corresponding to the cultivation process as described in the context of the bioreactor 200.

Figure 4A:
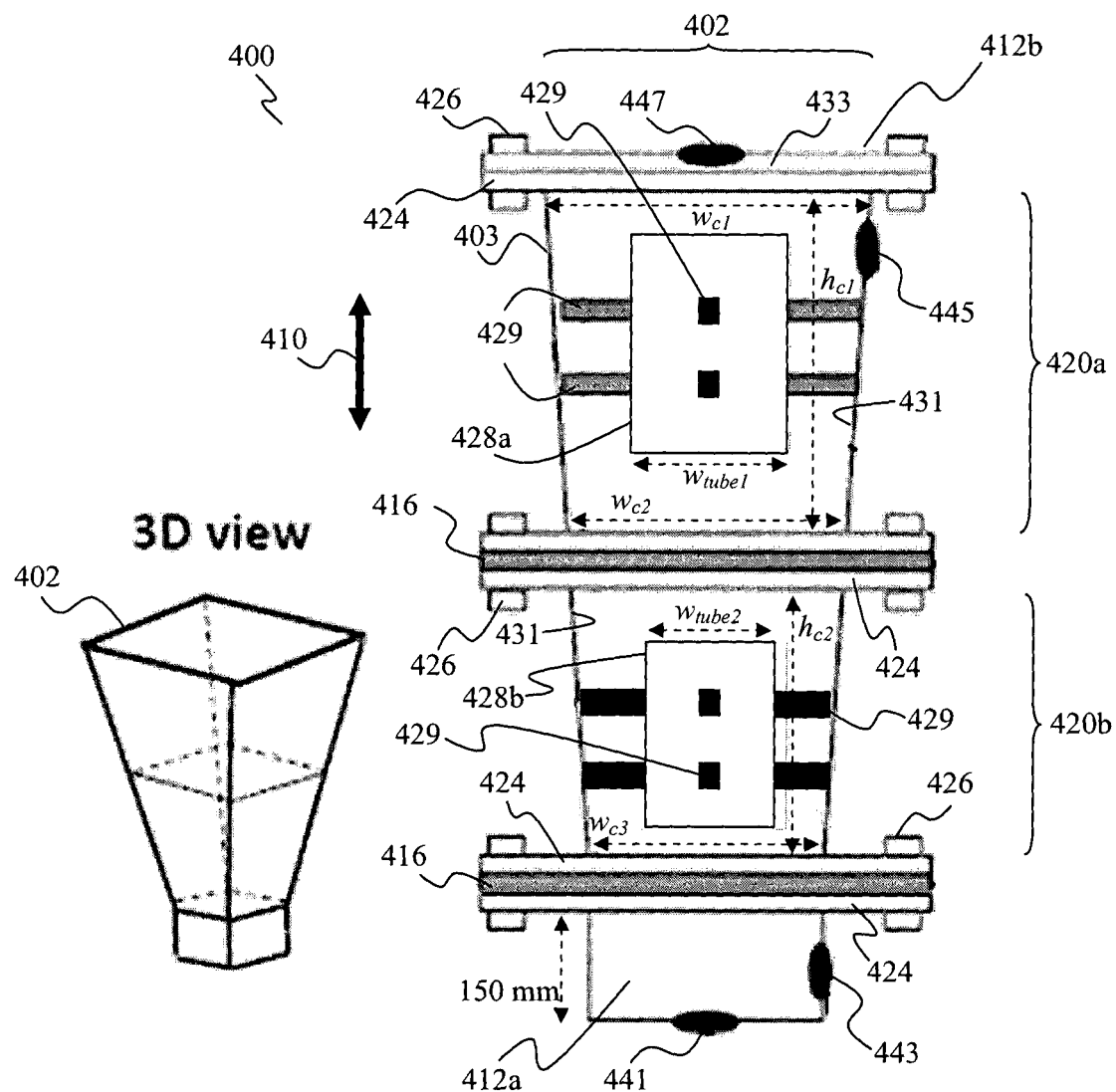
FIG. 4A shows a schematic diagram of a two-stage bioreactor, according to various embodiments.

FIG. 4A shows a two-stage bioreactor 400 with a vessel 402 having a square cross sectional shape, in a cross-sectional view and a 3D perspective view, according to various embodiments. The vessel 402 has a longitudinal axis, as represented by the double-headed arrow 410, which a circumferential wall 403 extends around the longitudinal axis 410. The vessel 402 has a base 412a and a top 412b. At least a portion of the vessel 402 has a tapering cross section adapted to flare (e.g. taper outwardly) in a direction along the longitudinal axis 410, from the base 412a towards the top 412b.

The vessel 402 is provided with two gas-liquid distributors 416 along the length of the vessel 402. The gas-liquid distributors 416 are spaced apart and act as dividers to define two compartments 420a, 420b, within the vessel 402 along the longitudinal axis 410. Each gas-liquid distributor 416 may have a thickness of about 10 mm, but not so limited.

Each gas-liquid distributor 416 includes one or more orifices (not shown), defined through the gas-liquid distributor 416 to allow fluid communication between the compartments 420a, 420b. Each gas-liquid distributor 416 may be as described later in the context of the embodiment shown in FIG. 4C.

Each gas-liquid distributor 416 may be held between two flanges 424 extending from the circumferential wall 403 of the vessel 402, where the gas-liquid distributor 416 and the two flanges 424 are secured together by securing means (e.g. bolts) 426 to hold and secure the gas-liquid distributor 416. The two flanges 424 overlap around the peripheral edges of the gas-liquid distributor 416 respectively on the top and bottom faces of the gas-liquid distributor 416. Each flange 424 may have a thickness of about 10 mm, but not so limited.

The compartment 420a may have a cross sectional dimension or width, $w_{c1}$, at the top, of about 600 mm, a cross sectional dimension or width, $w_{c2}$, at the bottom, of about 520 mm, and a height, $h_{c1}$, of about 1000 mm. The compartment 420b may have a cross sectional dimension or width at the top substantially similar to $w_{c2}$, a cross sectional dimension or width, $w_{c3}$, at the bottom, of about 488 mm, and a height, $h_{c2}$, of about 400 mm.

A respective draft tube 428a, 428b may be provided in each compartment 420a, 420b. Each draft tube 428a, 428b may have a square cross section. The cross sectional dimension or width, $w_{tube1}$, of the draft tube 428a in the compartment 420a, may be about 500 mm, which is larger than the cross sectional dimension or width, $w_{tube2}$, of the draft tube 428b in the compartment 420b, which may be about 400 mm.

Each draft tube 428a, 428b may have its hollow core at least substantially aligned with the orifice(s) of the corresponding gas-liquid distributors 416. The draft tubes 428a, 428b may be arranged in a concentric square configuration. The draft tubes 428a, 428b may be attached to support structures 429 that are in turn attached or fixed to the inner side wall 431 of the vessel 402.

A cover 433 may be provided over the top of the compartment 420a to seal the vessel 402. A gasket or O-ring (not shown) may be provided at portion of the cover 433 overlapping with the flange 424 at the top of the compartment 420a to minimise any liquid leakage.

The vessel 402 may include a liquid inlet of a diameter of about 25.4 mm (1 inch) with a 1 inch NPT (National Pipe Thread) fitting 441 and a gas inlet of a diameter of about 25.4 mm (1 inch) with a 1 inch NPT (National Pipe Thread) fitting 443. The vessel 402 may further include a liquid outlet of a diameter of about 25.4 mm (1 inch) with a 1 inch NPT (National Pipe Thread) fitting 445 and a gas outlet, formed through the cover 433, of a diameter of about 25.4 mm (1 inch) with a 1 inch NPT (National Pipe Thread) fitting 447.

Figure 4B:
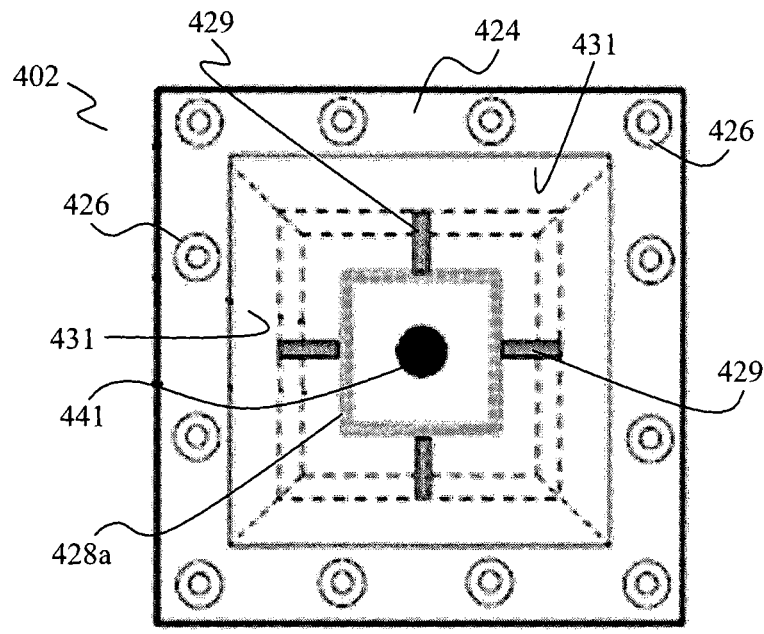
FIG. 4B shows a schematic top view of the bioreactor of the embodiment of FIG. 4A.

FIG. 4B shows a schematic top view of the bioreactor of the embodiment of FIG. 4A. For clarity purposes and to show the interior of the vessel 402 to the base 412a of the vessel 402, the cover 433, the gas-liquid distributors 416, and the draft tube 428b are not illustrated in FIG. 4B. In FIG. 4B, the dashed lines are shown to illustrate the tapering configuration of the inner side wall 431, and therefore also that of the circumferential wall 403 of the vessel 402.

Figure 4C:
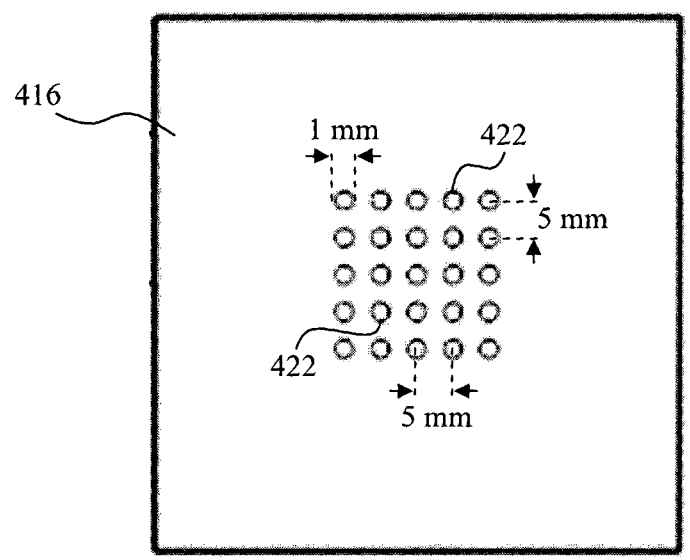
FIG. 4C shows a schematic top view of a gas-liquid distributor, according to various embodiments.

FIG. 4C shows a schematic top view of a gas-liquid distributor 416, according to various embodiments. The gas-liquid distributor 416 includes a plurality of orifices 422, defined through the gas-liquid distributor 416. As shown in FIG. 4C, there may be 25 orifices 422 arranged in a 5×5 square array. However, it should be appreciated that any number of orifices 422 may be provided and/or any arrangement of the orifices 422, for example in a regular array or randomly. In various embodiments, the number and/or the arrangement of the orifices 422 of a gas-liquid distributor 416 may depend on the cross sectional width (or diameter) of the draft tube arranged over and/or beneath the gas-liquid distributor 416 such that the orifices 422 may be at least substantially aligned with the hollow core of the draft tube(s), for example aligned within the boundary of the circumferential wall of the draft tube(s).

Each orifice 422 may have a diameter of about 1 mm and the orifices may have a square pitch distance of about 5 mm.

It should be appreciated that the dimensions described in the context of FIGS. 4A to 4C are non-limiting examples and therefore it should be appreciated that other dimensions may be provided.

It should be appreciated that the configuration of the vessel 402, including the associated components and dimensions, as described, may be similarly applicable to the vessel 302, and vice versa.

Figure 5:
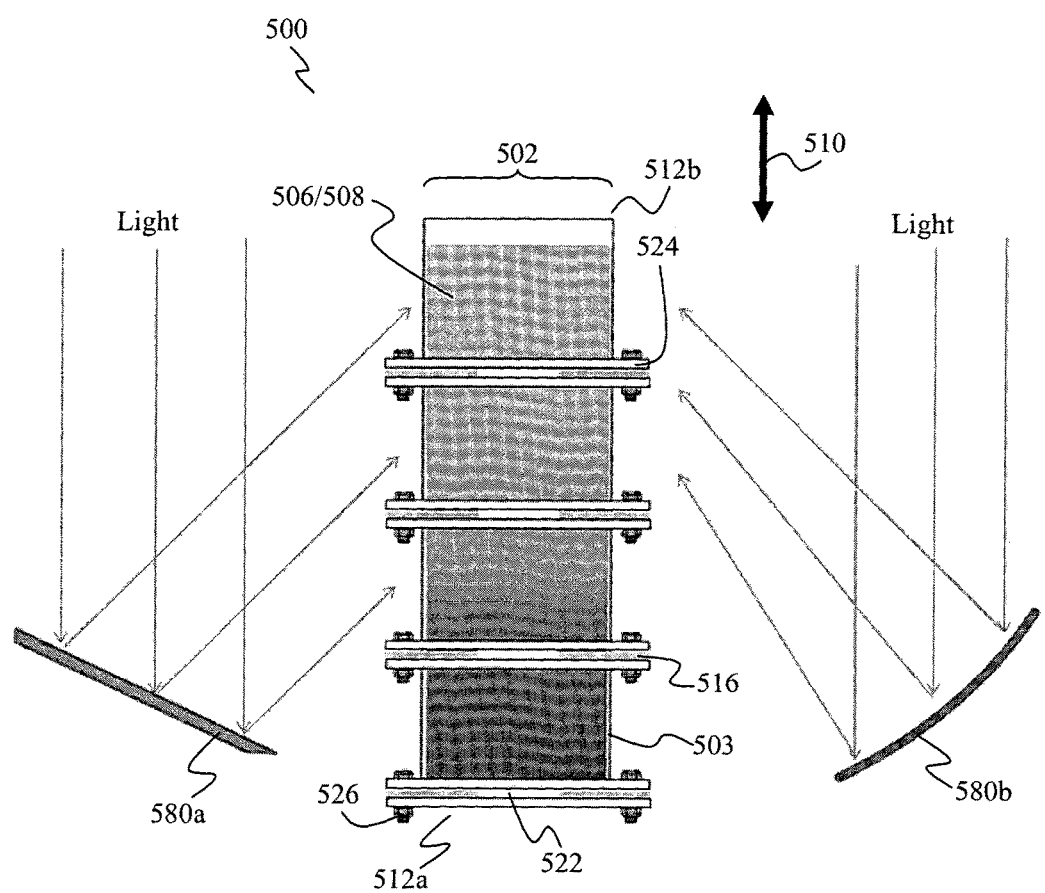
FIG. 5 shows a schematic diagram of a bioreactor, according to various embodiments.

FIG. 5 shows a schematic diagram of a bioreactor 500 for growing photoautotrophic organisms 506, according to various embodiments. The bioreactor 500 includes a vessel 502 having a longitudinal axis, as represented by the double-headed arrow 510, which a circumferential wall 503 extends around the longitudinal axis 510. The vessel 502 may have a circular or a square cross section. The vessel 502 has a base 512a and a top 512b. The photoautotrophic organisms (e.g. microalgae) 506 for cultivation, provided or suspended in a liquid (e.g. a culture medium) 508, are contained within the vessel 502. The vessel 502 may have a uniform cross section and/or may be made of transparent acrylic.

The vessel 502 is provided with a number of gas-liquid distributors 516 along the length of the vessel 502. The gas-liquid distributors 516 are spaced apart and act as dividers to define a plurality of compartments within the vessel 502. The gas-liquid distributors 516 may include one or more orifices (collectively represented by 522). The gas-liquid distributors 516 may be similar to that as described in the context of the bioreactor 300 or the bioreactor 400.

Each gas-liquid distributor 516 may be held between two flanges 524 extending from the circumferential wall 503 of the vessel 502, where the gas-liquid distributor 516 and the two flanges 524 are secured together by securing means (e.g. bolts) 526 to hold and secure the gas-liquid distributor 516. The two flanges 524 may lie around the peripheral edges of the gas-liquid distributor 516, respectively on the top and bottom faces of the gas-liquid distributor 516. The flange 524 may be similar to that as described in the context of the bioreactor 300 or the bioreactor 400.

The bioreactor 500 further includes one or more external reflective surfaces or light directors, for example mirror(s) to reflect light (as represented by the line arrows) incident on the mirrors towards the vessel 502 in order to provide variable or uneven light distribution of light intensity within the different compartments or stages of the vessel 502. The external mirror(s) or light directors (e.g. mirrors) therefore may be employed to provide the required amount of distribution of light intensity within the different compartments of the vessel 502 so as to provide variable light intensity corresponding to the different stages of the cultivation process. The light may be sunlight and/or light provided by one or more light sources.

In this arrangement, the mirror(s) may be arranged to direct light towards the vessel 502 so as to provide a small distribution of light intensity towards the base 512a of the vessel 502 where the photoautotrophic organisms 506 are in the initial growth period, with the proportion of the distribution of the light intensity gradually or progressively increasing towards the top 512b of the vessel where the photoautotrophic organisms 506 are in the final growth period. This may provide an optimum distribution of light intensity corresponding to the growth stage of the photoautotrophic organisms 506 in the vessel 502 as the photoautotrophic organisms 506 move through the vessel 502 from the base 512a towards the top 512b as photoautotrophic organisms 506 grow.

While not shown, other features or components (e.g. draft tube, inlet, outlet, pressure gauge), including dimensions, as described in the context of the bioreactor 200 or the bioreactor 300 or the bioreactor 400 may be provided in the bioreactor 500.

The cultivation process may be carried out based on a similar approach corresponding to the cultivation process as described in the context of the bioreactor 200 or the bioreactor 300.

In one embodiment, the bioreactor may include a mirror 580a having a flat surface arranged on one or more sides of the vessel 502, and a mirror 580b having a concave surface curved away from the vessel 502 arranged on one or more sides of the vessel 502. The mirror 580b having a concave surface may provide a focused light radiation towards the vessel 502.

In various embodiments, a plurality of mirrors 580a and/or a plurality of mirrors 580b may be arranged to direct light to different portions or compartments of the vessel 502 or different predetermined areas of the circumferential wall 503.

It should be appreciated that other arrangements of the mirrors may be provided, for example an arrangement having only mirror(s) of the type of mirror 580a or the type of mirror 580b.

Figure 6:
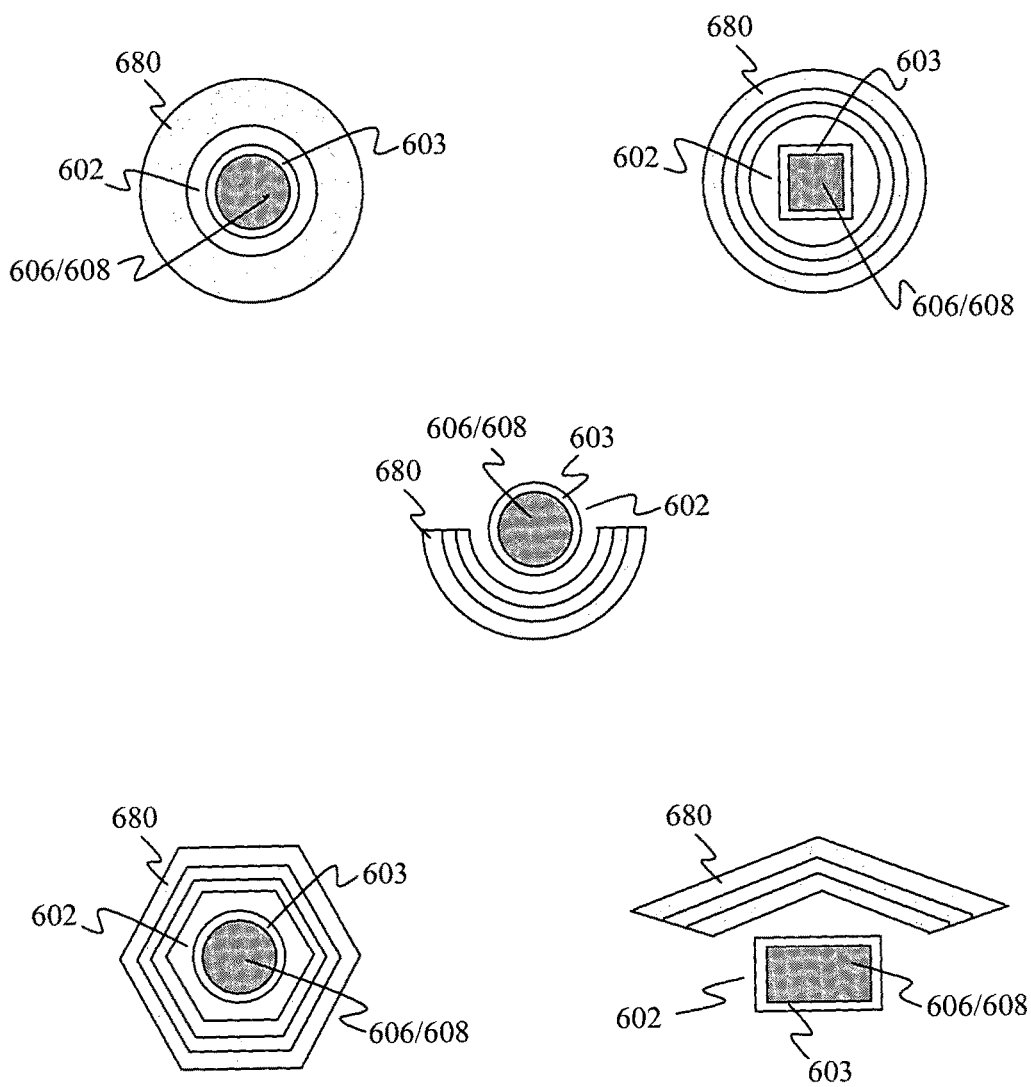
FIG. 6 shows schematic top views of bioreactors with different cross sectional shapes, with different arrangements of reflective surfaces, according to various embodiments.

The reflective surface(s) or mirror(s) employed may be arranged on one or more sides of the vessel, at least partially surrounding the vessel, where different non-limiting arrangements are shown in FIG. 6, from a top view. As shown in FIG. 6, various embodiments may provide a bioreactor having a vessel 602 with a circumferential wall 603, and configured to receive photoautotrophic organisms 606 in a liquid (e.g. a culture medium) 608. The vessel 602 may have any cross sectional shape, including but not limited to a circle, a square, a rectangle, a hexagon or any other polygonal shape. One or more mirrors 680 may be arranged to partially surround or entirely surround the vessel 602. The mirror(s) 680 may include a plane mirror having a flat surface and/or a concave mirror having a curved surface.

It should be appreciated that features and/or components that are described in the context of an embodiment may correspondingly be applicable to the other embodiments. As a non-limiting example, the bioreactor 300 may include one or more light panels as described in the context of the embodiment of FIG. 2. As a further non-limiting example, the bioreactor 300 having a tapered configuration may include one or more reflective surfaces or mirrors as described in the context of the embodiments of FIGS. 5 and 6, thereby allowing a broad range of bioreactor design flexibilities for providing variable distribution of the light intensity corresponding to different stages of the growth of the photoautotrophic organisms.

The cultivation of photoautotrophic organisms, the lumostatic protocol employed and the associated results will now be described by way of the following non-limiting examples based on the cultivation of photoautotrophic organisms in the bioreactor (photobioreactor) of the embodiment as shown in FIG. 2. The bioreactor used has a circular cross-section.

In addition to light being used as a parameter for the lumostatic operation, the chlorophyll a of the photoautotrophic organisms was also used as a parameter for the lumostatic operation. Chlorophyll is a component of the chloroplast that is responsible for photosynthesis. Among various forms of cholorophyll, chlorophyll a is the principal pigment for the conversion of light energy to chemical energy, and which has a positive relation with the photosynthesis rate.

The photoautotrophic organisms used were of the microalgae species *Chlorella* sp. (American Type Culture Collection, ATCC 14854). The cells of *Chlorella* sp. ATCC 14854 were grown in modified R-medium. The compositions of the modified R-medium are as shown in Table 1. The modified R-medium may improve the specific growth rate and prevent or minimise nutrient limitation.

TABLE 1

| Composition | Concentration (mg/L) |
|---|---|
| $Na_3C_6H_5O_7 \cdot 2H_2O$ (sodium citrate) | 500 |
| $FeCl_3 \cdot 6H_2O$ (ferric chloride hexahydrate) | 10 |
| $CaCl_2 \cdot 2H_2O$ (calcium chloride dihydrate) | 53 |
| $MgSO_4 \cdot 7H_2O$ (magnesium sulfate heptahydrate) | 900 |
| $NH_4NO_3$ (ammonia nitrate) | 600 |
| $KH_2PO_4$ (potassium dihydrogen phosphate) | 200 |
| $K_2HPO_4 \cdot 3H_2O$ (potassium phosphate trihydrate) | 393 |
| $NaC_2H_3O_2$ (sodium acetate) | 1804.7 |
| $H_3BO_3$ (boric acid) | 1.0 |
| $ZnSO_4 \cdot 7H_2O$ (zinc sulfate heptahydrate) | 1.0 |
| $MnSO_4 \cdot H_2O$ (manganese sulfate monohydrate) | 0.303 |
| $CoCl_2 \cdot 6H_2O$ (cobalt chloride hexahydrate) | 0.2 |
| $Na_2MoO_4 \cdot 2H_2O$ (sodium molybdate dihydrate) | 0.2 |
| $CuSO_4 \cdot 5H_2O$ (copper sulfate pentahydrate) | 0.0625 |

During the cultivation process, the light intensity was varied by adjusting the number of light bulbs (224, FIG. 2) and the distance between the panels (208a, 208b, FIG. 2) and the vessel (202, FIG. 2). The gas source supplied was a mixture of compressed air and compressed carbon dioxide flowed upstream through the vessel. All cultivation processes were conducted at a carbon dioxide concentration of about 2% (v/v) and a total flow rate at about 0.26 vvm (volume of gas per volume of liquid medium per minute). A substantially constant culture temperature of 28° C. was maintained throughout the cultivation period using a temperature controller (Polyscience, Ill., USA).

Prior to each cultivation, inoculums for cultivation in the photobioreactor were prepared by aseptically transferring microalgae from agar plates to 250 mL flasks containing 100 mL of modified R-medium. The microalgae were then incubated in a shaker incubator (Spectra Teknik, 200B) under a constant light intensity of 100 μmol/m²s at 100 rpm and 28° C. for about 2 days. The inoculums of the microalgae cells were harvested at the exponential growth phase from the flask using centrifugation at 2500 rpm for 10 minutes and re-suspended in 1.5 L of the modified R-medium to provide an initial cell concentration of $10^6$ cell/mL. The 1.5 L microalgae culture was then transferred to the photobioreactor and the microalgae were allowed to adapt to the culture medium (208, FIG. 2) in the vessel (202, FIG. 2) for a duration of 12 hours.

Measurements such as optical density, temperature, pH and chlorophyll a content were taken every 6 hours. A maximum of 5 mL of 0.1 M HCl was added when the pH exceeds 8.0. Single drop of corn oil was added to the culture medium when foaming was observed. The culture time lasted about 7 days (120±10 hours) until the stationary phase was achieved where the cell concentration reached constant.

The microalgae biomass dry weight was determined by centrifugation of a known volume of the microalgae culture at 3000 rpm for 10 minutes, and formed into pellets. The cell pellets were then washed with distilled water twice, and dried in a freeze dryer (Christ Alpha 1-2LD Plus) to a constant weight. The cell concentration was determined by cell counting of a sample with a known dilution factor using a cell count chamber hemocytometer (Fisher USA) and an optical microscope (Fisher).

The biomass dry weight and cell concentration during the course of a cultivation period were correlated to the optical densities at 680 nm ($OD_{680}$) of the microalgae samples. The microalgae sample was placed in a PMMA (poly(methyl methacrylate)) 1 cm path-length cuvette and the $OD_{680}$ was measured using a Nicolet Evolution 500 UV-Visible Spectrophotometer (Thermo Electron Corporation, England). When necessary, the microalgae sample was diluted with deionized (DI) water to an $OD_{680}$ range of 0.1-1.0 to maintain measurement accuracy. Conversions of $OD_{680}$ to biomass dry weight and cell concentration were performed based on linear regression equations.

The pH of the microalgae culture was measured by a pH probe (Orion 3-in-1 pH electrode Spectra-Teknik SG). The three points calibration was performed on the pH probe using the calibration buffers of pH 4.1, pH 7.0 and pH 10.0 (Fisher USA) at the beginning of each cultivation run.

Chlorophyll a content was measured by the spectrophotometric method. 5 ml of microalgae sample was centrifuged at 5000 rpm for 10 minutes, and formed into pellets, and washed with PBS (phosphate buffered saline) buffer (8 g NaCl, 0.2 g KCl, 1.44 g $Na_2HPO_4$, 0.24 g $KH_2PO_4$) twice. The cell pellets were then mixed with 5 ml of pure methanol, heated in a 70° C. water bath for 10 minutes and centrifuged at 5000 rpm for 10 minutes. The supernatant absorbance was measured at wavelengths of 665 nm and 750 nm. The chlorophyll a content, Chla, may then be calculated using Equation 1 below.

$$Chla(mg/L) = 13.9 \times (AB_{665} - AB_{750}) \quad \text{(Equation 1)},$$

where $AB_{665}$ is the absorbance at the wavelength of 665 nm and $AB_{750}$ is the absorbance at the wavelength of 750 nm.

The incident light intensity was measured at the inside surface of the vessel of the photobioreactor in the absence of culture medium using a quantum sensor (LI-190SL by LI-COR Inc., USA) equipped with a data logger (LI-250A by LI-COR Inc., USA). An average surface light intensity was calculated based on an 8-point measurement, each 45° apart along the surface of the photobioreactor.

An image analysis approach was utilized to obtain the light distribution profiles inside the bioreactor vessel under various cultivation conditions in the presence of the culture medium, based on the top-view images of the bioreactor. At each cell concentration, a set of images at various incident light intensities ranging from 82 μmol/m²s to 590 μmol/m²s were taken using a digital camera (Canon 450D). The digital camera was mounted on a tripod stand. The aperture size, shutter speed, and distance between the camera lens and the surface of the culture medium were maintained constant for all conditions. Gas flow was temporarily ceased while an image was taken to prevent or minimise distortion of liquid surface due to bursting of bubbles.

Image processing was first carried out by cropping the raw camera image to contain only the circular photobioreactor portion. A pre-developed image analysis algorithm, as described in Hossain et al., Industrial & Engineering Chemistry Research 48, pages 10136-10146, 2009, the entire disclosure of which is incorporated herein by reference, was then utilized to convert the cropped image from the RGB (red-green-blue) space into grayscale based on the equation below:

$$\text{Grayscale value} = (0.222 \times \text{Red}) + (0.707 \times \text{Green}) + (0.071 \times \text{Blue}) \quad \text{(Equation 2)}.$$

Figure 7A:
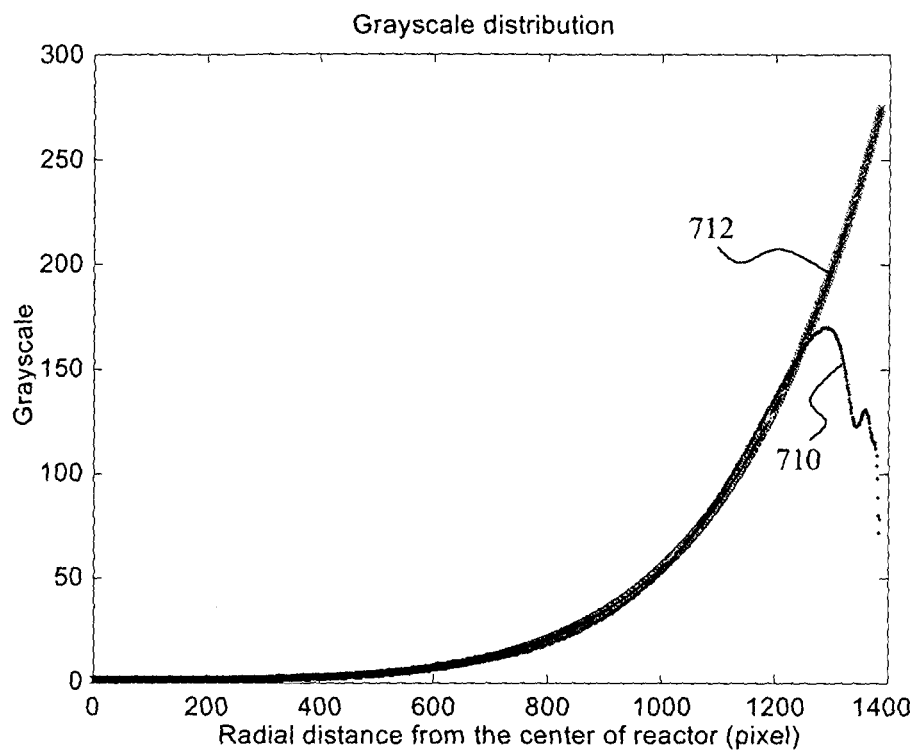
FIG. 7A shows a plot of converted radial grayscale distribution obtained from image analysis of a camera image.
Figure 7B:
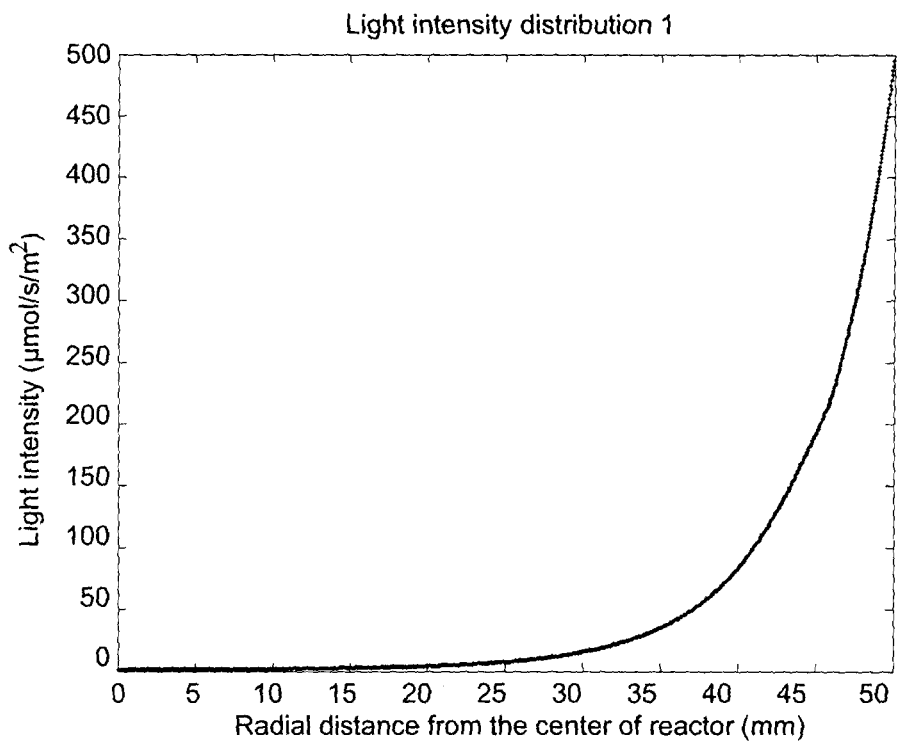
FIG. 7B shows a plot of radial light intensity distribution in a bioreactor obtained from sensor measurements.

Each image pixel in the grayscale image may be represented by a value between 0 (Black) and 255 (White) in grayscale. A radial grayscale distribution may be obtained by averaging all the grayscale values at the same radial locations, and the results may be as shown in FIG. 7A. As shown in FIG. 7A, it may be observed that the radial grayscale value increased from the center and reached a maximum value just before the photobioreactor surface due to the presence of meniscus, the results being represented by 710. A Matlab curve fitting toolbox was applied to obtain a more rational grayscale distribution with an exponential function, as represented by 712. Calibration may be obtained by comparing the grayscale values obtained from the image analysis and the surface light intensity measurements by quantum sensor under various light intensities, which may be as shown in FIG. 7B for the radial light intensity distribution in the photobioreactor.

The specific average light intensity, Q, defined as the amount of light energy received per cell per unit time (μmol/cell·s) in the photobioreactor vessel was selected as one of the light controlling parameters. For a known light intensity distribution, Q may be determined by:

$$Q = \frac{1}{C_{cell}} \frac{\int_A I(r) H\, dA}{V}, \quad \text{(Equation 3)}$$

where I(r) is the radial light intensity distribution, H is the height of the culture medium in the photobioreactor vessel, A is the cross-sectional area in the photobioreactor vessel, V is the volume of the culture medium and $C_{cell}$ is the cell concentration.

The specific average light intensity, Q, is a function of the surface light intensity, $I_0$, and the cell concentration, $C_{cell}$. A model to predict or estimate Q was developed based on the results of 304 set of measurements using a combination of 19 cell concentrations ranging from $4.73 \times 10^7$ cell/mL to $5.07 \times 10^8$ cell/mL and 16 surface light intensities ranging from 0 μmol/m²s to 590 μmol/m²s. The model may be derived by first determining Q based on the 304 set of measurements using Equation 3 in order to generate an empirical equation which may be used to determine Q, based on $I_0$ and $C_{cell}$. The empirical equation (Equation 4) will be described later.

Cultivation of *Chlorella* sp. was performed in the photobioreactor under constant surface light intensities of 82 μmol/m²s, 260 μmol/m²s, 368 μmol/m²s and 590 μmol/m²s. Comparisons of microalgae growth were made in terms of the maximum biomass dry weight and chlorophyll a content.

Figure 8A:
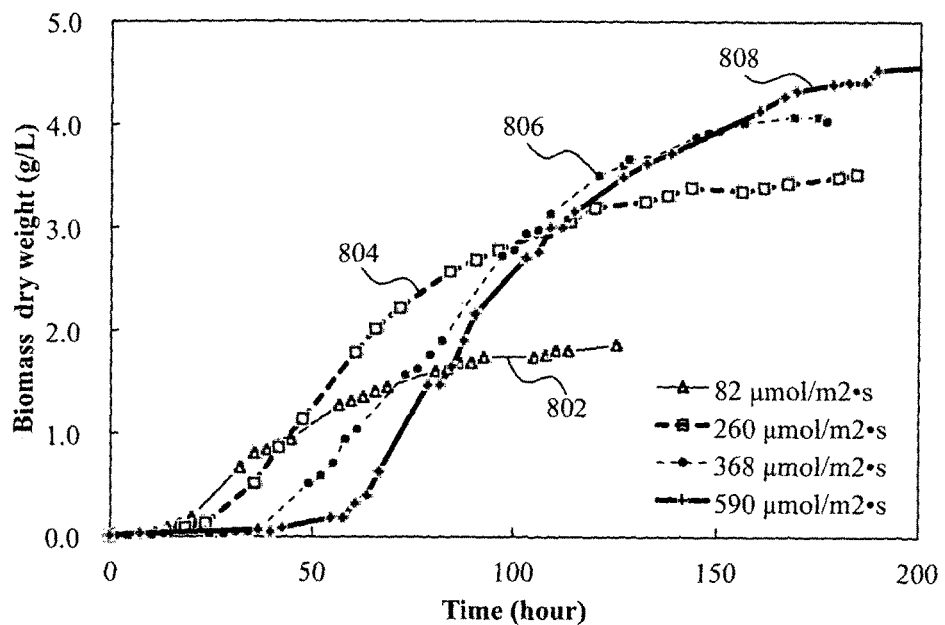
FIG. 8A shows a plot of cultivation characteristics of *Chlorella* sp. under various constant light intensities, in terms of the biomass growth.

The growth curves of *Chlorella* sp. under the four constant light intensities are shown in FIG. 8A, for light intensities of about 82 μmol/m²s (growth curve represented by 802), about 260 μmol/m²s (growth curve represented by 804), about 368 μmol/m²s (growth curve represented by 806) and about 590 μmol/m²s (growth curve represented by 808). The maximum biomass dry weight was the lowest under the constant light intensity of 82 μmol/m²s, which was about 1.87 g/L. The biomass dry weight increased with an increase in the light intensity and reached a maximum of about 4.60 g/L at 590 μmol/m²s.

In addition to the maximum biomass dry weight, the duration of the lag phase at the beginning of the cultivation process, during which the microalgae adapted to the culture medium and where the microalgae growth rate may be low, was also affected by the light intensity. An increase in the light intensity was found to increase the lag phase duration and to reduce the microalgae productivity. This may be because the initial cell concentrations for all the cultivation processes performed were so low that the four constant light intensities used inhibited the photosynthetic rate of the microalgae cells. In addition to photoinhibition, the microalgae cells also underwent photoacclimation, in order to cope with high light intensities and maintain a constant photosynthetic efficiency. The higher the light intensity, the longer the photoacclimation time and consequently a longer lag phase duration.

During the exponential growth period, the growth rates of the microalgae showed an increasing trend with an increase in the light intensities. Therefore, the optimal light intensity to be employed for the cultivation of the microalgae requires a balance between the lag phase duration and the growth rate during the exponential phase.

Figure 8B:
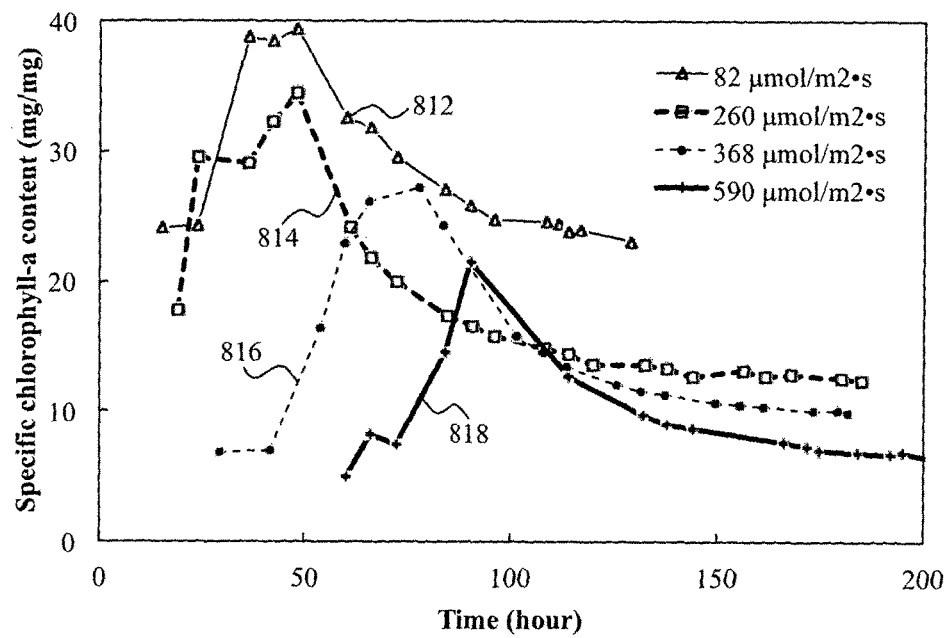
FIG. 8B shows a plot of cultivation characteristics of *Chlorella* sp. under various constant light intensities, in terms of the specific chlorophyll a content.

The specific chlorophyll a contents (i.e. chlorophyll a content per biomass dry weight) corresponding to the cultivation processes under constant light intensities were determined, and the results are as shown in FIG. 8B for light intensities of about 82 μmol/m²s (curve represented by 812), about 260 μmol/m²s (curve represented by 814), about 368 μmol/m²s (curve represented by 816) and about 590 μmol/m²s (curve represented by 818). The specific chlorophyll a content may be used to assess the process of photoinhibition and photolimitation.

It may be observed that the specific chlorophyll a contents for the different light intensities rose steadily until a maximum and then decreased monotonically. As chlorophyll a is an indicator of photosynthetic rate, the point of maximum specific chlorophyll a content may be considered to correspond to the condition of optimal photosynthetic rate of the *Chlorella* sp. microalgae cells.

It may also be observed that both the maximum specific chlorophyll a content and the specific chlorophyll a content at the end of the cultivation period decreased with an increase in the light intensity. This may provide an indication of photoacclimation through which the microalgae cells alleviated photoinhibition by decreasing the ratio of chlorophyll to carbon. The microalgae cells may produce smaller chlorophyll antenna sizes and less chlorophyll a contents at a high light intensity as a protective mechanism to minimize the photon absorption and reduce photoinhibition.

Lumostatic cultivation may be carried out, relying on the supply of light intensity at an optimal level or distribution based on the cell concentration. The optimal light intensity may be considered to be the light intensity at which the average light intensity received per cell may allow the microalgae cells to reach the maximum photosynthetic rate.

Figure 9:
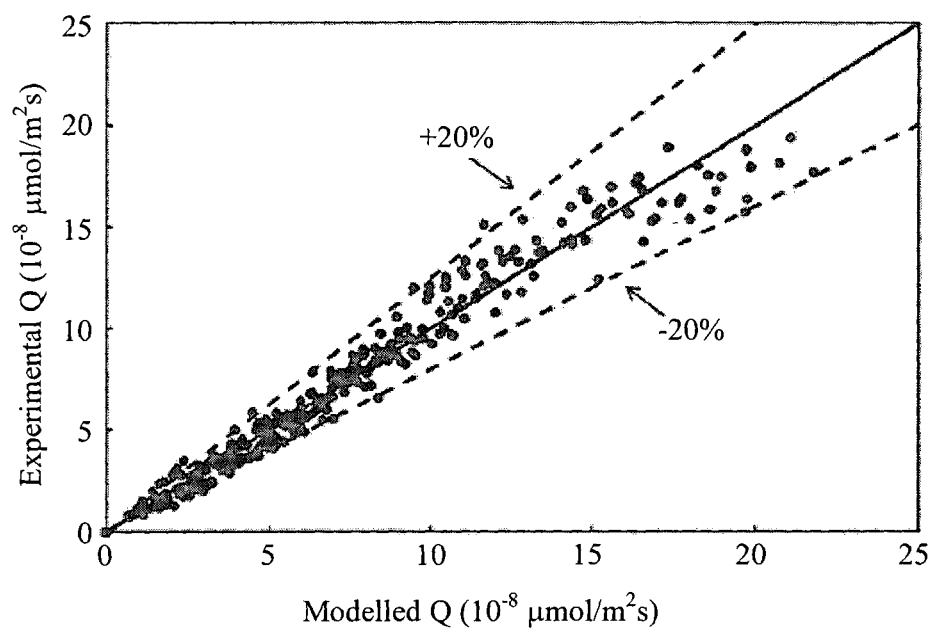
FIG. 9 shows a parity plot for the specific average light intensity.
Figure 10A:
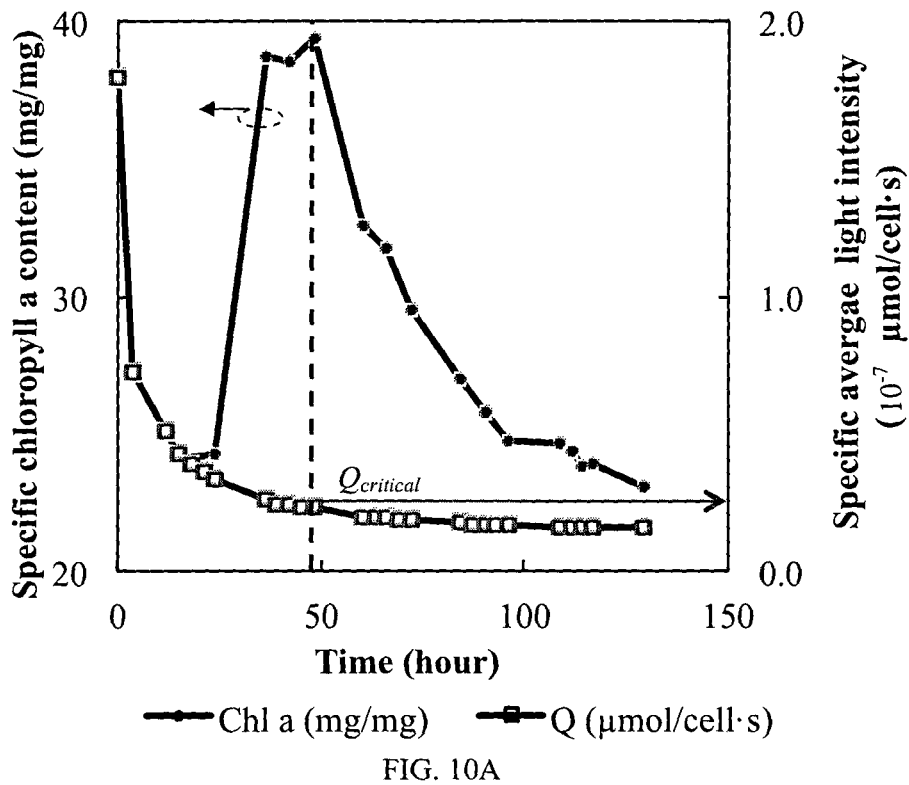
FIGS. 10A to 10D show plots of specific chlorophyll a content and specific average light intensity as a function of cultivation time for different cell concentrations.
Figure 10B:
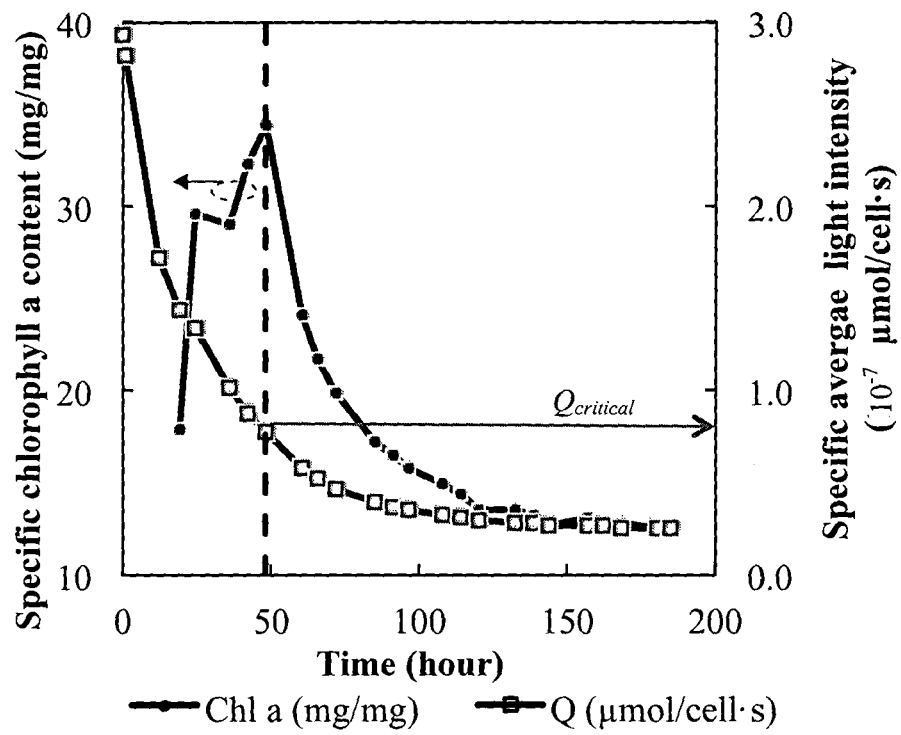
Figure 10C:
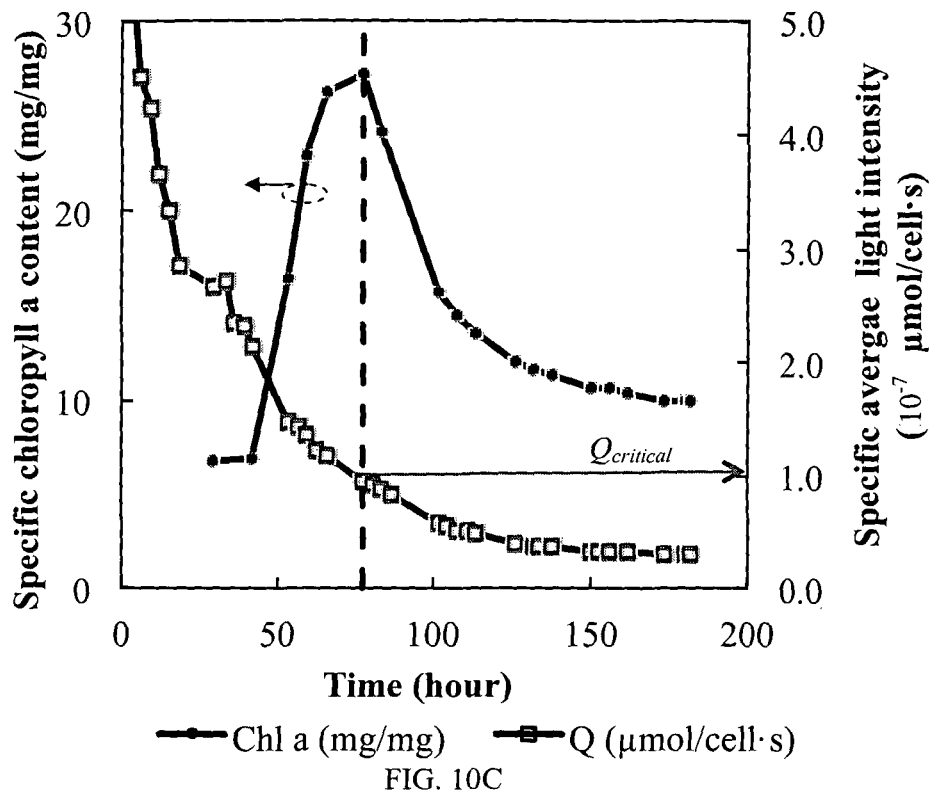
Figure 10D:
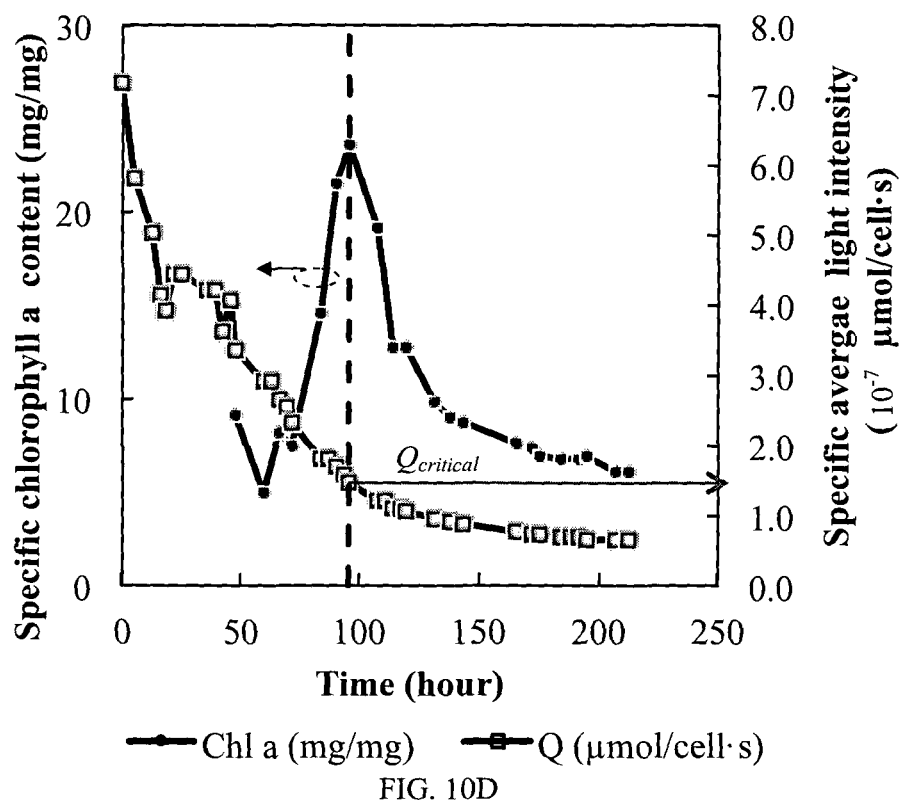

Image analysis was performed to obtain the light distribution profiles from the 304 sets of various combinations of 19 cell concentrations and 16 light intensities. Equation 3 was then applied to determine the specific average light intensity, Q, under various combinations of the cell concentrations and the light intensities. It was determined that Q has an exponential relationship with the surface light intensity, $I_0$, and inversely proportional to the cell concentration, $C_{cell}$. An empirical equation may be derived to model the function, as expressed in Equation 4.

$$Q = \frac{e^{a \ln(I_0+1)^b - 1} e^{c C_{cell} + d C_{cell}}}{C_{cell}}, \quad \text{(Equation 4)}$$

where a, b, c, and d are empirical constants, equal to $7.89 \times 10^{-8}$, $5.70$, $-4.61 \times 10^{-9}$ and $0.12$, respectively. A parity plot as shown in FIG. 9 illustrates that Equation 4 is able to predict or estimate Q at any least substantially accurately at any given cell concentration and light intensity.

Based on the determination of the change in specific chlorophyll a content in a cultivation cycle (FIG. 8B), the specific average light intensity, Q, at which the specific chlorophyll a content reaches a maximum may be considered as a critical point for *Chlorella* sp. to be photolimited, or in other words, *Chlorella* sp. may experience photolimitation effect when the specific average light intensity is below this critical point, $Q_{critical}$. The critical specific average light intensity, $Q_{critical}$, may be determined from a correlation between the specific chlorophyll a content and the specific average light intensity, Q, on the same figure. As shown in FIGS. 10A to 10D, four values of $Q_{critical}$ were determined for different cell concentrations, $C_{cell}$. With a known $Q_{critical}$ and $C_{cell}$, may be determined by using Equation 4 and the results are as shown in Table 2.

TABLE 2

| $C_{cell}$ ($\times 10^8$ cell/mL) | $Q_{critical}$ ($\times 10^{-8}$ µmol/cell s) | $I_{critical}$ (µmol/m²s) |
|---|---|---|
| 1.11 | 2.31 | 82 |
| 1.58 | 7.56 | 260 |
| 1.71 | 10.01 | 368 |
| 1.91 | 14.52 | 590 |

Based on the results, a lumostatic strategy was employed, based upon the maintenance of $I_{critical}$ at all $C_{cell}$. The relationship between $I_{critical}$ and $C_{cell}$ as shown in Table 2 was determined to follow an exponential function as expressed in Equation 5.

$$I_{critical} = 5.26 e^{2.47 C_{cell}} \quad \text{(Equation 5)}.$$

Throughout the cultivation period, the light intensity, I, supplied was maintained at a level within 50% of $I_{critical}$. The light intensity was kept at a minimum value of 6 µmol/m²s at the beginning of the cultivation period for all starting cell concentrations. The light intensity was also maintained at the minimum value of 6 µmol/m²s at the beginning of the lumostatic cultivation process. As the cell concentration increased, the corresponding $I_{critical}$ also increased. When $I_{critical}$ was more than 50% higher than the light intensity, I, supplied, I was increased to about 150% of $I_{critical}$. The step-increase procedure of the light intensity, I, was continued until the end of the cultivation period or when the light intensity, I, reached the supply limit of the light sources used.

Figure 11:
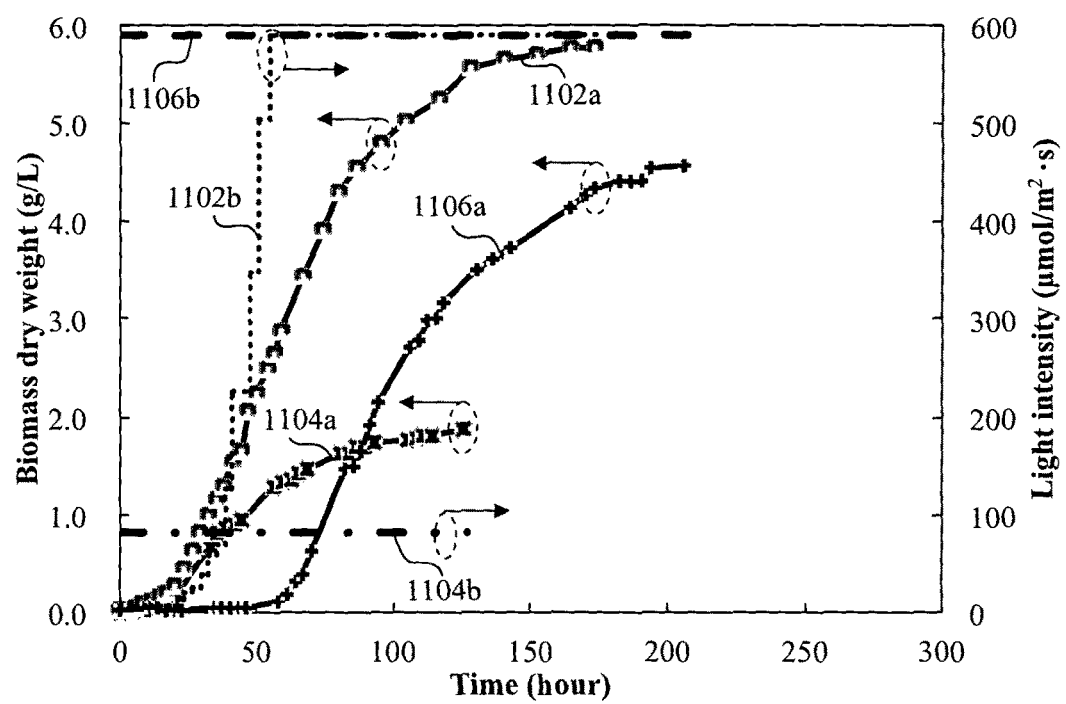
FIG. 11 shows a plot of the relationship between the growth curve of *Chlorella* sp. and the supplied light intensity, based on the lumostatic approach.

FIG. 11 shows a plot of the relationship between the growth curve 1102a of *Chlorella* sp. and the supplied light intensity 1102b, based on the lumostatic strategy. For comparison purposes, the growth curve 1104a of *Chlorella* sp. corresponding to a constant light intensity of 82 µmol/m²s 1102b, and the growth curve 1106a of *Chlorella* sp. corresponding to a constant light intensity of 590 µmol/m²s 1106b are also shown. As shown in FIG. 11, the growth of *Chlorella* sp. using the lumostatic approach was superior to the constant light intensity approach in both the growth rate and the maximum biomass dry weight obtained. Using the lumostatic approach, a biomass dry weight up to about 5.78 g/L was achieved.

Table 3 shows a comparison of the lag phase duration, the exponential phase duration and the productivity using various cultivation approaches. It may be observed that the lag phase duration was maintained at a minimum in the lumostatic operation, similar to that corresponding to a constant light intensity of 82 µmol/m²s. This suggests that the initial light intensity of 6 µmol/m²s supplied at the beginning of the cultivation process based on the lumostatic approach has low photoinhibition on the microalgae cells. The cells required a relatively short time to adapt to the cultivation environment and thus the photosynthetic capacity was enhanced. In addition, the lumostatic cultivation process was able to sustain a longer exponential phase duration than that of the constant light intensity approaches. A long exponential phase duration was favorable to achieve a high productivity as shown in Table 3. The lumostatic operation yielded the highest cell productivity of about 1.29 g/L-day, as compared to the cultivation processes based on constant light intensities.

TABLE 3

| Light intensity (µmol/m²s) | Lag phase duration (hour) | Exponential phase duration (hour) | Productivity (g/L day) |
|---|---|---|---|
| 82 | 17 | 40 | 0.67 |
| 260 | 27 | 44 | 0.74 |
| 368 | 39 | 69 | 0.70 |
| 590 | 58 | 72 | 0.65 |
| Lumostatic | 17 | 87 | 1.29 |

The lumostatic strategy employed was based on the relationship between $I_{critical}$ and $C_{cell}$ as shown in Table 2. During the lumostatic cultivation process, the light intensity supplied was up to 590 µmol/m²s, even when the cell concentration was higher than $2.0 \times 10^8$ cell/mL. However, it should be appreciated that a higher light intensity may be applied during the lumostatic cultivation process, as and when the cell concentration increases during the process. Using a higher light intensity beyond 590 µmol/m²s when the cell concentration is higher than $2.0 \times 10^8$ cell/mL so as to optimise the light intensity corresponding to an increase in the cell concentration may produce a longer exponential growth phase duration, a higher productivity and a higher biomass dry weight.

It should be appreciated that while the lumostatic cultivation approach has been described in the context of a closed bioreactor of various embodiments, such an approach may also be applied in open pond systems where natural sunlight may be utilised, where for example the light intensity of the midday sunlight is approximately 2000-2200 µmol/m²s, and proper screening may be provided to control the distribution of the light intensity received within the pond.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A bioreactor for growing photoautotrophic organisms, the bioreactor comprising:
   a vessel configured to receive the photoautotrophic organisms, the vessel having a longitudinal axis, which a circumferential wall extends around said axis, wherein said circumferential wall is translucent so as to enable light to enter the vessel from outside the bioreactor for acting on the photoautotrophic organisms, wherein said vessel has a base for positioning said vessel on a surface and a top provided on an end opposite to the base when seen along said axis, a device for providing an uneven distribution of light intensity of the light within said vessel along said axis, the uneven distribution of the light intensity comprising a distribution of the light intensity within said vessel that increases along the circumferential wall, towards the top of the vessel along said axis, wherein a circumference of said circumferential wall increases from said base towards said top, one or more spaced apart dividers arranged to define a plurality of compartments within the vessel along said axis, wherein each divider has at least one orifice defined through the divider for fluid communication between the plurality of compartments, and a plurality of draft tubes respectively arranged in the compartments of the plurality of compartments, wherein:

each compartment of the plurality of compartments comprises a respective draft tube of the plurality of draft tubes;

the respective draft tube is configured to be aligned with a respective divider such that a liquid medium and a gas that pass through the at least one orifice of the respective divider is distributed to the core of the draft tube, thereby inducing internal circulation of the liquid medium and the gas through the core of the draft tube, outwardly from the top of the draft tube and also inwardly into the interior of the draft tube from the bottom of the draft tube;

the draft tube is configured to impede light penetration to the interior of the draft tube.

2. A bioreactor according to claim 1, wherein a degree of transmissivity to light of the translucent surface of said circumferential wall varies along said axis.

3. A bioreactor according to claim 1, wherein the circumferential wall is made of a translucent material selected from the group consisting of glass, quartz and acrylic plastic.

4. A bioreactor according to claim 1, wherein said device for providing an uneven distribution of the intensity within said vessel along said axis comprises at least one mirror positioned outside the vessel for directing light towards a predetermined area of said translucent circumferential wall or towards a predetermined translucent area of said circumferential wall so as to provide the uneven distribution of the light intensity within said vessel along said axis.

5. A bioreactor according to claim 4, wherein said at least one mirror has a concave shape arranged to curve away from said circumferential wall of said vessel.

6. A bioreactor according to claim 4, wherein said at least one mirror is arranged to at least partially surround said circumferential wall of said vessel.

7. A bioreactor according to claim 1, wherein said device for providing an uneven distribution of the light intensity comprises a light filtering layer on said circumferential wall of said vessel, wherein said light filtering layer has a transmissivity to light that varies along said axis so as to provide the uneven distribution of the light intensity within said vessel along said axis.

8. A bioreactor according to claim 1, wherein said device for providing an uneven distribution of the light intensity comprises a filter arrangement positioned outside the vessel, wherein said filter arrangement has a transmissivity to light that varies along said axis so as to provide the uneven distribution of the light intensity within said vessel along said axis.

9. A bioreactor according to claim 1, wherein said device for providing an uneven distribution of the light intensity comprises at least one light source positioned outside the vessel for supplying light towards a predetermined area of said translucent circumferential wall or towards a predetermined translucent area of said circumferential wall so as to provide the uneven distribution of the light intensity within said vessel along said axis.

10. A bioreactor according to claim 9, wherein said device for providing an uneven distribution of the light intensity comprises a plurality of light sources positioned outside the vessel for supplying light towards a plurality of predetermined areas of said translucent circumferential wall or towards a plurality of predetermined translucent areas of said circumferential wall, wherein said light sources are spaced from said translucent circumferential wall or said circumferential wall of said vessel at respective distances that vary along said axis so as to provide the uneven distribution of the light intensity within said vessel along said axis.

11. A bioreactor according to claim 9, wherein said device for providing an uneven distribution of the light intensity comprises a plurality of light sources positioned outside the vessel for supplying light towards a plurality of predetermined areas of said translucent circumferential wall or towards a plurality of predetermined translucent areas of said circumferential wall, wherein the number of light sources for supplying light towards the predetermined areas of said translucent circumferential wall or towards the predetermined translucent areas of said circumferential wall, varies along said axis so as to provide the uneven distribution of light intensity within said vessel along said axis.

12. A bioreactor according to claim 1,
wherein the compartments have respective light intensities, and the light intensity within one compartment of the plurality of compartments is different than the light intensity of a subsequent compartment of the plurality of compartments along said axis so as to provide the uneven distribution of the light intensity within said vessel along said axis.

13. A bioreactor according to 12, wherein each compartment has a height that is different than a height along said axis of a subsequent compartment of the plurality of compartments.

14. A bioreactor according to claim 12, wherein said at least one orifice has a diameter of between about 1 mm and about 10 mm.

15. A bioreactor according to claim 12, wherein each divider has a plurality of orifices, and wherein two adjacent orifices of the plurality of orifices have a spacing that is between about 1 mm and about 10 mm.

16. A bioreactor according to claim 1, wherein each draft tube has an inner diameter that is different than an inner diameter of a subsequent one of the draft tubes in a subsequent compartment of the plurality of compartments.

17. A bioreactor according to claim 1, wherein said circumferential wall has a shape selected from the group consisting of a circle, an ellipse, a square, a rectangle and a hexagon.

18. A bioreactor according to claim 1, wherein said light intensity is between about 50 mol/m$^2$s and about 1000 mol/m$^2$s.

* * * * *